United States Patent
Hickman et al.

(10) Patent No.: US 9,267,936 B2
(45) Date of Patent: *Feb. 23, 2016

(54) SYNTHETIC MAMMALIAN NEUROMUSCULAR JUNCTION AND METHOD OF SCREENING FOR A CANDIDATE DRUG THEREON

(71) Applicant: University of Central Florida Research Foundation, Inc., Orlando, FL (US)

(72) Inventors: James Hickman, Orlando, FL (US); Xiufang Guo, Oviedo, FL (US)

(73) Assignee: University of Central Florida Research Foundation, Orlando, FL (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/453,207

(22) Filed: Aug. 6, 2014

(65) Prior Publication Data

US 2014/0349884 A1 Nov. 27, 2014

Related U.S. Application Data

(63) Continuation of application No. 13/696,396, filed as application No. PCT/US2011/035585 on May 6, 2011, now Pat. No. 8,835,165, which is a continuation-in-part of application No. 12/765,996, filed on Apr. 23, 2010, now Pat. No. 8,815,584.

(60) Provisional application No. 61/332,003, filed on May 6, 2010, provisional application No. 61/171,958, filed on Apr. 23, 2009.

(51) Int. Cl.
| | |
|---|---|
| *C12N 5/16* | (2006.01) |
| *C12N 5/071* | (2010.01) |
| *C12N 5/00* | (2006.01) |
| *G01N 33/50* | (2006.01) |
| *G01N 33/487* | (2006.01) |
| *G01N 33/68* | (2006.01) |

(52) U.S. Cl.
CPC .......... *G01N 33/5058* (2013.01); *C12N 5/0697* (2013.01); *G01N 33/48728* (2013.01); *G01N 33/6872* (2013.01); *G01N 33/6887* (2013.01); *C12N 2500/90* (2013.01); *C12N 2501/01* (2013.01); *C12N 2501/105* (2013.01); *C12N 2501/13* (2013.01); *C12N 2501/385* (2013.01); *C12N 2501/41* (2013.01); *C12N 2501/58* (2013.01); *C12N 2502/081* (2013.01); *C12N 2502/1335* (2013.01); *C12N 2533/20* (2013.01); *C12N 2535/10* (2013.01); *G01N 2500/10* (2013.01)

(58) Field of Classification Search
USPC ........................................ 435/347, 368, 373
See application file for complete search history.

(56) References Cited

U.S. PATENT DOCUMENTS

| | | | |
|---|---|---|---|
| 5,442,510 | A | 8/1995 | Schwartz |
| 5,682,899 | A | 11/1997 | Nashef |
| 5,948,621 | A | 9/1999 | Turner |
| 6,866,383 | B2 | 3/2005 | Naik |
| 6,916,541 | B2 | 7/2005 | Pantano |
| 6,935,165 | B2 | 8/2005 | Bashir |
| 7,384,786 | B2 | 6/2008 | Freyman |
| 7,541,146 | B2 | 6/2009 | Lewis |
| 7,579,189 | B2 | 8/2009 | Freyman |
| 7,691,629 | B2 | 4/2010 | Johe |
| 7,860,563 | B2 | 12/2010 | Foreman |
| 7,923,015 | B2 | 4/2011 | Vazquez-Martinez |
| 7,927,671 | B2 | 4/2011 | Kato |
| 8,071,319 | B2 | 12/2011 | Metzger |
| 8,178,602 | B2 | 5/2012 | Mao |
| 8,318,488 | B1 | 11/2012 | Bohlen |
| 8,318,489 | B2 | 11/2012 | Davidson |
| 8,318,951 | B2 | 11/2012 | Olson |
| 2003/0065452 | A1 | 4/2003 | Hickman |
| 2003/0144823 | A1 | 7/2003 | Fox |
| 2003/0211542 | A1 | 11/2003 | Lee |
| 2006/0105457 | A1 | 5/2006 | Rameshwar |
| 2006/0259992 | A1 | 11/2006 | Koren |
| 2007/0015138 | A1 | 1/2007 | Barlow |
| 2007/0117217 | A1 | 5/2007 | Lal |

(Continued)

FOREIGN PATENT DOCUMENTS

| | | |
|---|---|---|
| CA | 2788905 | 2/2011 |
| CA | 2798777 | 5/2011 |

(Continued)

OTHER PUBLICATIONS

Chua SJ, et al. (2009) Neural progenitors, neurons and oligodendrocytes from human umbilical cord blood cells in a serum-free, feeder-free cell culture. Biochem Biophys Res Commun. 379(2):217-221.
Davis H, et al. (2012) Small Molecule Induction of Human Umbilical Stem Cells into MBP-positive Oligodendrocytes in a Defined Three-Dimensional Environment. ACS Chem Neurosci. 3(1):31-39.
Gaztañaga L, et al. (2012) Mechanisms of cardiac arrhythmias. Rev Esp Cardiol (Engl Ed). 65(2):174-85.
Mars T. (2008) Effects of LIF on Neuromuscular Junction Formation in Co-Cultures of Rat Spinal Cord Explant and Human Muscle. Croatica Chimica Acta, 81(1): 177-182.
Morimoto S, et al. (1984) Dependence of conduction velocity on spike interval during voluntary muscular contraction in human motor units. Eur J Appl Physiol Occup Physiol. 53(3):191-195.

(Continued)

*Primary Examiner* — Kagnew H Gebreyesus
*Assistant Examiner* — Paul Martin
(74) *Attorney, Agent, or Firm* — Meunier Carlin & Curfman LLC

(57) ABSTRACT

A method for forming neuromuscular junctions includes forming functional neuromuscular junctions between motoneurons and muscle cells by co-culturing one or more human motoneurons and one or more human muscle cells in a substantially serum-free medium. A synthetic mammalian neuromuscular junction includes a human motoneuron functionally linked to a human muscle cell in a substantially serum-free medium. An artificial substrate may be used to support the one or more neuromuscular junctions.

13 Claims, 4 Drawing Sheets

(56) References Cited

U.S. PATENT DOCUMENTS

| | | |
|---|---|---|
| 2007/0129447 A1 | 6/2007 | Sra |
| 2007/0212723 A1 | 9/2007 | Dudley |
| 2008/0124789 A1 | 5/2008 | Hickman |
| 2008/0227137 A1 | 9/2008 | Zhang |
| 2009/0029463 A1 | 1/2009 | Collins |
| 2009/0227469 A1 | 9/2009 | Conklin |
| 2009/0239940 A1 | 9/2009 | Del Monte |
| 2009/0305319 A1 | 12/2009 | Baudenbacher |
| 2011/0250682 A1 | 10/2011 | Hickman |
| 2012/0122728 A1 | 5/2012 | Hickman |
| 2012/0128639 A1 | 5/2012 | Hickman |
| 2013/0096888 A1 | 4/2013 | Hickman |

FOREIGN PATENT DOCUMENTS

| | | |
|---|---|---|
| EP | 2434896 | 4/2012 |
| EP | 2435585 | 4/2012 |
| EP | 2531910 | 12/2012 |
| EP | 2585171 | 5/2013 |
| WO | WO 01/29206 | 4/2001 |
| WO | WO 2005/033264 | 4/2005 |
| WO | WO 2007/044314 | 4/2007 |
| WO | WO 2010/127280 | 11/2010 |
| WO | WO 2010/138679 | 12/2010 |
| WO | WO 2010/138782 | 12/2010 |
| WO | WO 2011/097574 | 8/2011 |
| WO | WO 2011/133985 | 10/2011 |
| WO | WO 2012/158923 | 11/2012 |
| WO | WO 2013/013206 | 1/2013 |
| WO | WO 2014/028940 | 2/2014 |

OTHER PUBLICATIONS

Nash MP, et al. (2004) Electromechanical model of excitable tissue to study reentrant cardiac arrhythmias. Prog Biophys Mol Biol. 85(2-3):501-522.
Nistor GI, et al. (2005) Human embryonic stem cells differentiate into oligodendrocytes in high purity and myelinate after spinal cord transplantation. Glia. 49(3):385-396.
Nugaeva N, et al. (2005) Micromechanical cantilever array sensors for selective fungal immobilization and fast growth detection. Biosens Bioelectron. 21(6):849-856.
Response to Final Rejection filed Apr. 3, 2014 for U.S. Appl. No. 12/661,323, filed Mar. 15, 2010 (Hickman et al.—inventors) (11 pages).
Notice of Allowance mailed Apr. 3, 2014 for U.S. Appl. No. 12/765,996, filed Apr. 23, 2010 (Hickman et al.—inventors) (6 pages).
Response to Final Rejection with Terminal Disclaimer filed Mar. 14, 2014 for U.S. Appl. No. 12/765,996, filed Apr. 23, 2010 (Hickman et al.—inventors) (69 pages).
Response to Non-Final Rejection with Terminal Disclaimer filed Apr. 18, 2014 for U.S. Appl. No. 13/102,672, filed May 6, 2011 (Hickman et al.—inventors) (12 pages).
Non-Final Rejection mailed Mar. 6, 2014 for U.S. Appl. No. 13/102,672, filed May 6, 2011 (Hickman et al.—inventors) (15 pages).
Response to Non-Final Rejection filed Apr. 17, 2014 for U.S. Appl. No. 13/696,396 (Hickman et al.—inventors) (10 pages).
Response to Non-Final Rejection filed Mar. 10, 2014 for U.S. Appl. No. 13/322,911, filed Feb. 2, 2012 (Hickman et al.—inventors) (11 pages).
Rule 1.312 Amendment filed Apr. 30, 2014 for U.S. Appl. No. 12/788,732, filed May 27, 2010 (Hickman et al.—Inventors) (3 pages).
Notice of Allowance and Fee(s) Due mailed Apr. 22, 2014 for U.S. Appl. No. 12/788,732, filed May 27, 2010 (Hickman et al.—Inventors) (5 pages).
Response to Non-Final Rejection filed on Apr. 10, 2014 for U.S. Appl. No. 12/938,701, filed Nov. 3, 2010 (Molnar et al.—inventors) (12 pages).

Communication pursuant to Rule 71(3) EPC issued Mar. 14, 2014 for European Patent Application No. 11740493.9, which claims priority to PCT/US2011/023921 filed on Feb. 7, 2011 (Applicant—University of Central Florida Research Foundation // Inventors—James Hickman, et al) (61 pages).
Communication pursuant to Article 94(3) EPC issued on Mar. 7, 2014 for European Patent Application No. 10781190.3-1402 (Hickman et al.—Inventors // University of Central Florida Research Foundation, Inc.—Applicant) (4 pages).
Extended European Search Report mailed Jan. 3, 2014 for European Patent Application No. 10781254.7, which claims priority to PCT/US2010/036505 filed May 28, 2010 (Hickman et al.—Inventors // University of Central Florida Research Foundation, Inc.—Applicant) (9 pages).
International Search Report and Written Opinion issued on May 15, 2014 for PCT/US2014/013903 filed on Jan. 30, 2014 (Hickman et al.—Inventors // University of Central Florida Research Foundation, Inc.—Applicant) (15 pages).
U.S. Appl. No. 12/117,339, J.J. Hickman.
U.S. Appl. No. 12/145,810, J.J. Hickman.
U.S. Appl. No. 12/661,323, J.J. Hickman.
U.S. Appl. No. 12/765,399, J.J. Hickman.
U.S. Appl. No. 12/765,996, J.J. Hickman.
U.S. Appl. No. 12/788,732, J.J. Hickman.
U.S. Appl. No. 12/938,701, J.J. Hickman.
Preliminary Amendment filed Jul. 10, 2012 for U.S. Appl. No. 12/117,339, filed May 8, 2008 (Hickman et al—inventors)(5 pages).
Non-Final Office Action issued Aug. 24, 2012 for U.S. Appl. No. 12/117,339, filed May 8, 2008 (Hickman et al—inventors)(10 pages).
Response to Non-Final Office Action filed Jan. 24, 2013 for U.S. Appl. No. 12/117,339, filed May 8, 2008 (Hickman et al—inventors)(8 pages).
Non-Final Office Action issued Oct. 11, 2013 for U.S. Appl. No. 12/117,339, filed May 8, 2008 (Hickman et al—inventors)(10 pages).
Restriction Requirement issued Jun. 7, 2011 for U.S. Appl. No. 12/145,810, filed Jun. 25, 2008 (Hickman et al—inventors)(5 pages).
Response to Restriction Requirement filed Jul. 5, 2011 for U.S. Appl. No. 12/145,810, filed Jun. 25, 2008 (Hickman et al—inventors)(7 pages).
Non-Final Office Action issued Aug. 31, 2011 for U.S. Appl. No. 12/145,810, filed Jun. 25, 2008 (Hickman et al—inventors)(8 pages).
Response to Non-Final Office Action filed Jan. 31, 2012 for U.S. Appl. No. 12/145,810, filed Jun. 25, 2008 (Hickman et al—inventors)(13 pages).
Final Office Action issued Apr. 9, 2012 for U.S. Appl. No. 12/145,810, filed Jun. 25, 2008 (Hickman et al—inventors)(7 pages).
Notice of Abandonment issued on Oct. 19, 2012 for U.S. Appl. No. 12/145,810, filed Jun. 25, 2008 (Hickman et al—inventors)(2 pages).
Restriction Requirement issued Sep. 27, 2012 for U.S. Appl. No. 12/661,323, filed Mar. 15, 2010 (Hickman et al—inventors)(10 pages).
Response to Restriction Requirement filed Nov. 17, 2012 for U.S. Appl. No. 12/661,323, filed Mar. 15, 2010 (Hickman et al—inventors)(7 pages).
Non-Final Office Action issued Mar. 13, 2013 for U.S. Appl. No. 12/661,323, filed Mar. 15, 2010 (Hickman et al—inventors)(14 pages).
Response to Non-Final Office Action filed Jul. 12, 2013 for U.S. Appl. No. 12/661,323, filed Mar. 15, 2010 (Hickman et al—inventors)(11 pages).
Restriction Requirement issued Aug. 7, 2012 for U.S. Appl. No. 12/765,996, filed Feb. 23, 2010 (Hickman et al—inventors)(6 pages).
Response to Restriction Requirement filed on Sep. 7, 2012 for U.S. Appl. No. 12/765,996, filed Feb. 23, 2010 (Hickman et al—inventors)(7 pages).
Non-Final Office Action issued Nov. 13, 2012 for U.S. Appl. No. 12/765,996, filed Feb. 23, 2010 (Hickman et al—inventors)(11 pages).
Response to Non-Final Office Action filed on Apr. 12, 2013 for U.S. Appl. No. 12/765,996, filed Feb. 23, 2010 (Hickman et al—inventors)(70 pages).

(56) References Cited

OTHER PUBLICATIONS

Notice of Non-Compliant Amendment issued Apr. 19, 2013 for U.S. Appl. No. 12/765,996, filed Feb. 23, 2010 (Hickman et al—inventors)(2 pages).
Letter Withdrawing a Notice of Non-Compliant Amendment issued Apr. 25, 2013 for U.S. Appl. No. 12/765,996, filed Feb. 23, 2010 (Hickman et al—inventors)(2 pages).
Restriction Requirement issued Oct. 3, 2012 for U.S. Appl. 13/102,672, filed May 6, 2011 (Hickman et al—inventors)(7 pages).
Response to Restriction Requirement filed Nov. 16, 2012 for U.S. Appl. No. 13/102,672, filed May 6, 2011 (Hickman et al—inventors)(6 pages).
Preliminary Amendment filed Nov. 6, 2012 for U.S. Appl. No. 13/696,396, filed Nov. 6, 2012 (Hickman, et al—inventors)(4 pages).
Restriction Requirement issued Sep. 30, 2013 for U.S. Appl. No. 13/696,396, filed Nov. 6, 2012 (Hickman, et al.—inventors)(11 pages).
International Search Report issued Jul. 28, 2011 for PCT Application No. PCT/US2011/035585, which published as WO 2011/133985 on Oct. 27, 2011 (Applicant: University of Central Florida Research Foundation // Inventors—James Hickman, et al)(2 Pages).
Written Opinion issued Jul. 28, 2011 for PCT Application No. PCT/US2011/035585, which published as WO 2011/133985 on Oct. 27, 2011 (Applicant: University of Central Florida Research Foundation // Inventors—James Hickman, et al)(4 pages).
International Preliminary Report on Patentability issued Oct. 23, 2012 for PCT Application No. PCT/US2011/035585, which published as WO 2011/133985 on Oct. 27, 2011 (Applicant: University of Central Florida Research Foundation // Inventors—James Hickman, et al)(5 pages).
Communication pursuant to Rules 161(2) and 162 EPC issued on Dec. 18, 2012 for Patent Application No. 11772857.6, which claims priority to PCT/US11/35585, which published as WO 2011/133985 on Oct. 27, 2011 (Applicant: University of Central Florida Research Foundation // Inventors—James Hickman, et al)(2 pages).
Response to Communication pursuant to Rules 161(2) and 162 EPC filed Aug. 2, 2012 for European Patent Application No. 11772857.6, which claims priority to PCT/US11/35585, which published as WO 2011/133985 on Oct. 27, 2011 (Applicant: University of Central Florida Research Foundation // Inventors—James Hickman, et al).
Restriction Requirement issued Jul. 19, 2012 for U.S. Appl. No. 12/765,399, filed Apr. 22, 2010 (Hickman, et al—inventors)(7 pages).
Response to Restriction Requirement filed Aug. 17, 2012 for U.S. Appl. No. 12/765,399, filed Apr. 22, 2010 (Hickman, et al—inventors)(5 pages).
Non-Final Office Action issued Oct. 18, 2012 for U.S. Appl. No. 12/765,399, filed Apr. 22, 2010 (Hickman, et al—inventors)(9 pages).
Response to Non-Final Office Action filed Jan. 16, 2013 for U.S. Appl. No. 12/765,399, filed Apr. 22, 2010 (Hickman, et al—inventors)(49 pages).
Final Office Action issued Apr. 15, 2013 for U.S. Appl. No. 12/765,399, filed Apr. 22, 2010 (Hickman, et al—inventors)(7 pages).
Response to Final Office Action filed Aug. 15, 2013 for U.S. Appl. No. 12/765,399, filed Apr. 22, 2010 (Hickman, et al—inventors)(6 pages).
International Search Report issued Jul. 30, 2010 for PCT Application No. PCT/US2010/36336, which published as WO 2010/138679 on Dec. 2, 2010 (Applicant: University of Central Florida Research Foundation // Inventors—James Hickman, et al)(2 Pages).
Written Opinion issued Jul. 30, 2010 for PCT Application No. PCT/US2010/036336, which published as WO 2010/138679 on Dec. 2, 2010 (Applicant: University of Central Florida Research Foundation // Inventors—James Hickman, et al)(4 Pages).
International Preliminary Report on Patentability issued Nov. 29, 2011 for PCT Application No. PCT/US2010/036336, which published as WO 2010/138679 on Dec. 2, 2010 (Applicant: University of Central Florida Research Foundation // Inventors—James Hickman, et al)(5 Pages).
Preliminary Amendment filed Nov. 28, 2011 for U.S. Appl. No. 13/322,911, filed Nov. 28, 2011 (Hickman, et al—inventors)(4 pages).
Non-Final Office Action issued Sep. 10, 2013 for U.S. Appl. No. 13/322,911, filed Nov. 28, 2011 (Hickman, et al—inventors)(14 pages).
Communication conveying Extended European Search Report issued Jan. 22, 2013 for EP Application No. 10781190.3, which claims priority to PCT/US2010/036336 filed on May 27, 2010 (Applicant—University of Central Florida Research Foundation// Inventors—James Hickman et al.) (6 Pages).
Restriction Requirement issued Sep. 14, 2012 for U.S. Appl. No. 12/765,399, filed May 27, 2010 (Hickman, et al—inventors)(5 pages).
Response to Restriction Requirement filed Nov. 14, 2012 for U.S. Appl. No. 12/788,732, filed May 27, 2010 (Hickman, et al—inventors)(6 pages).
Non-Final Office Action issued Feb. 28, 2013 for U.S. Appl. No. 12/788,732, filed May 27, 2010 (Hickman, et al—inventors)(6 pages).
Response to Non-Final Office Action filed May 28, 2013 for U.S. Appl. No. 12/788,732, filed May 27, 2010 (Hickman, et al—inventors)(11 pages).
Final Office Action issued Sep. 16, 2013 for U.S. Appl. No. 12/788,732, filed May 27, 2010 (Hickman, et al—inventors)(5 pages).
International Search Report issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(2 Pages).
Written Opinion issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(5 Pages).
International Preliminary Report on Patentability issued Jul. 15, 2010 for PCT Application No. PCT/US2010/036505, which published as WO 2010/138782 on Dec. 2, 2010 (Applicant: University of Central Florida Research Foundation // Inventors—James Hickman and Hedvika Davis)(6 Pages).
Preliminary Amendment filed Nov. 28, 2011 for U.S. Appl. No. 13/322,903, filed Nov. 28, 2011 (Hickman and Davis—inventors)(4 pages).
Restriction Requirement issued Nov. 27, 2012 for U.S. Appl. No. 13/322,903, filed Nov. 28, 2011 (Hickman and Davis—inventors)(6 pages).
Response to Restriction Requirement filed Dec. 1, 2012 for U.S. Appl. No. 13/322,903, filed Nov. 28, 2011 (Hickman and Davis—inventors)(6 pages).
Non-Final Office Action issued Jan. 31, 2013 for U.S. Appl. No. 13/322,903, filed Nov. 28, 2011 (Hickman and Davis—inventors)(17 pages).
Response to Non-Final Office Action filed Jul. 31, 2013 for U.S. Appl. No. 13/322,903, filed Nov. 28, 2011 (Hickman and Davis—inventors)(15 pages).
Communication pursuant to Rules 161(2) and 162 EPC issued on Jan. 23, 2012 for European Patent Application No. 10781254.7, which claims priority to PCT/US2010/36505 filed on May 28, 2010 (Applicant—University of Central Florida Research Foundation// Inventors—James Hickman and Hedvika Davis )(2 pages).
Response to Communication pursuant to Rules 161(2) and 162 EPC filed Aug. 2, 2012 for European Patent Application No. 10781254.7, which claims priority to PCT/US2010/36505 filed on May 28, 2010 (Applicant—University of Central Florida Research Foundation// Inventors—James Hickman and Hedvika Davis )(5 pages).
Restriction Requirement issued Mar. 7, 2013 for U.S. Appl. No. 12/938,701, filed Nov. 3, 2010 (Hickman, et al—inventors)(7 pages).
Response to Restriction Requirement filed Apr. 8, 2013 for U.S. Appl. No. 12/938,701, filed Nov. 3, 2010 (Hickman, et al—inventors)(6 pages).

(56) References Cited

OTHER PUBLICATIONS

Non-Final Office Action issued Jun. 13, 2013 for U.S. Appl. No. 12/938,701, filed Nov. 3, 2010 (Hickman, et al—inventors)(8 pages).
Response to Non-Final Office Action filed Oct. 3, 2013 for U.S. Appl. No. 12/938,701, filed Nov. 3, 2010 (Hickman, et al—inventors)(8 pages).
International Search Report issued Jun. 7, 2011 for PCT Application No. PCT/US2011/023921, which published as WO 2011/097574 on Aug. 11, 2011 (Applicant: University of Central Florida Research Foundation // Inventors—James Hickman, et al)(3 Pages).
Written Opinion issued Jun. 7, 2011 for PCT Application No. PCT/US2011/023921, which published as WO 2011/097574 on Aug. 11, 2011 (Applicant: University of Central Florida Research Foundation // Inventors—James Hickman, et al)(5 Pages).
International Preliminary Report on Patentability issued Aug. 7, 2012 for PCT Application No. PCT/US2011/023921, which published as WO 2011/097574 on Aug. 11, 2011 (Applicant: University of Central Florida Research Foundation // Inventors—James Hickman, et al)(6 Pages).
Preliminary Amendment filed Aug. 1, 2012 for U.S. Appl. No. 13/576,442, filed Aug. 1, 2012 (Hickman, et al—inventors)(4 pages).
Communication pursuant to Rules 161(2) and 162 EPC issued on Oct. 10, 2012 for European Patent Application No. 11740493.9, which claims priority to PCT/US2011/023921 filed on Feb. 7, 2011 (Applicant—University of Central Florida Research Foundation// Inventors—James Hickman, et al)(2 pages).
Response to Communication pursuant to Rules 161(2) and 162 EPC issued on Oct. 10, 2012 for European Patent Application No. 11740493.9, which claims priority to PCT/US2011/023921 filed on Feb. 7, 2011 (Applicant—University of Central Florida Research Foundation// Inventors—James Hickman, et al)(4 pages).
Communication conveying Extended European Search Report issued Jul. 10, 2013 for EP Application No. 11740493.9, which claims priority to PCT/US2011/023921 filed on Feb. 7, 2011 (Applicant—University of Central Florida Research Foundation// Inventors—James Hickman, et al)(7 Pages).
International Search Report issued Oct. 16, 2012 for PCT Application No. PCT/US2012/038358, which published as WO 2012/158923 on Nov. 22, 2012 (Applicant: University of Central Florida Research Foundation // Inventors—James Hickman, et al)(4 Pages).
Written Opinion issued Oct. 16, 2012 for PCT Application No. PCT/US2012138358, which published as WO 2012/158923 on Nov. 22, 2012 (Applicant: University of Central Florida Research Foundation // Inventors—James Hickman, et al)(6 Pages).
Abbanat D, et al. (2003) Novel antibacterial agents for the treatment of serious Gram-positive infections. Expert Opin Investig Drugs. 12: 379-399.
Abdi H. (2003) Multivariate Analysis. Encyclopedia of Social Sciences Research Methods. M. Lewis-Beck, A. Bryman and T. Futing. Thousand Oaks (CA), Sage.
Adell A, et al. (2002) Origin and functional role of the extracellular serotonin in the midbrain raphe nuclei. Brain Res Brain Res Rev. 39: 154-180.
Agarwal A, et al. (2013) Microfluidic heart on a chip for higher throughput pharmacological studies. Lab Chip. 13: 3599-3608.
Ahem CA, et al. (2003) Ca2+ current and charge movements in skeletal myotubes promoted by the beta-subunit of the dihydropyridine receptor in the absence of ryanodine receptor type 1. Biophys J. 84: 942-959.
Ahmari SE, et al. (2000) Assembly of presynaptic active zones from cytoplasmic transport packets. Nat Neurosci. 3: 445-451.
Ahuja TK, et al. (2007) Hippocampal slice cultures integrated with multi-electrode arrays: A model for study of long-term drug effects on synaptic activity. Drug Development Research. 68: 84-93.
Ainscow EK and Brand MD. (1999) Internal regulation of ATP turnover, glycolysis and oxidative phosphorylation in rat hepatocytes. Eur J Biochem. 266: 737-749.
Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol. 38.
Akanda N, et al. (2009) Analysis of toxin-induced changes in action potential shape for drug development. J Biomol Screen. 14: 1228-1235.
Alabed YZ, et al. (2006) Neuronal responses to myelin are mediated by rho kinase. J Neurochem. 96: 1616-1625.
Albensi BC. (2003) A comparison of drug treatment versus electrical stimulation for suppressing seizure activity. Drug News Perspect. 16: 347-352.
Albert R and Othmer H. (2003) The topology of the regulatory interactions predicts the expression pattern of the segment polarity genes in *Drosophila melanogaster*. J Theor Biol. 223: 1-18.
Albert Y, et al. (2005) Transcriptional regulation of myotube fate specification and intrafusal muscle fiber morphogenesis. J Cell Biol. 169: 257-268.
Alexander SL, et al. (1989) an atomic-resolution atomic-force microscope implemented using an optical lever. J Appl Phys. 65: 164-167.
Al-Shanti N, et al. (2008) Beneficial synergistic interactions of TNF-alpha and IL-6 in C2 skeletal myoblasts—potential cross-talk with IGF system. Growth Factors. 26: 61-73.
Alsina B, et al. (2001) Visualizing synapse formation in arborizing optic axons in vivo: dynamics and modulation by BDNF. Nat Neurosci. 4: 1093-1101.
Alterio J, et al. (1990) Acidic and basic fibroblast growth factor mRNAs are expressed by skeletal muscle satellite cells.Biochem Biophys Res Commun. 166: 1205-1212.
Altmann L. (2000) Multielectrode recordings of synaptic plasticity in brain slices: A new method for the assessment of neurotoxic effects. European Journal of Neuroscience. 12: 29-29.
Amarenco P, et al. (2006) High-dose atorvastatin after stroke or transient ischemic attack. N Engl J Med. 355: 549-559.
Amit M. (2007) Feeder-layer free culture system for human embryonic stem cells. Methods Mol Biol. 407: 11-20.
Anderson DJ, et al. (1997) Cell lineage determination and the control of neuronal identity in the neural crest. Cold Spring Harb Symp Quant Biol. 62: 493-504.
Anderson JE, et al. (1991) Distinctive patterns of basic fibroblast growth factor (bFGF) distribution in degenerating and regenerating areas of dystrophic (mdx) striated muscles. Dev Biol. 147: 96-109.
Andersson H and van den Berg A. (2004) Microfabrication and microfluidics for tissue engineering: state of the art and future opportunities. Lab Chip. 4: 98-103.
Antzelevitch C. (2001) Transmural dispersion of repolarization and the T wave. Cardiovasc Res. 50: 426-431.
Antzelevitch C. (2005) Cardiac repolarization. The long and short of it. Europace. 7: 3-9.
Aracil A, et al. (2004) Proceedings of Neuropeptides 2004, the XIV European Neuropeptides Club meeting. Neuropeptides. 38: 369-371.
Archer JD, et al. (2006) Persistent and improved functional gain in mdx dystrophic mice after treatment with L-arginine and deflazacort. FASEB J. 20: 738-740.
Armstrong DL and Rossie S. (1999) Ion channel regulation. Introduction. Adv Second Messenger Phosphoprotein Res. 33: ix-xx.
Arnold HH and Winter B. (1998) Muscle differentiation: more complexity to the network of myogenic regulators. Curr Opin Genet Dev. 8: 539-544.
Arnone MI and Davidson EH. (1997) the hardwiring of development: organization and function of genomic regulatory systems. Development. 124: 1851-1864.
Arsic N, et al. (2004) Vascular endothelial growth factor stimulates skeletal muscle regeneration in vivo. Mol Ther. 10: 844-854.
Askanas V, et al. (1987) De novo neuromuscular junction formation on human muscle fibres cultured in monolayer and innervated by foetal rat spinal cord: ultrastructural and ultrastructural—cytochemical studies. J Neurocytol. 16: 523-537.
Asotra K and Macklin WB. (1993) Protein kinase C activity modulates myelin gene expression in enriched oligodendrocytes. J Neurosci Res. 34: 571-588.

(56) References Cited

OTHER PUBLICATIONS

Azzouz M, et al. (2004) VEGF delivery with retrogradely transported lentivector prolongs survival in a mouse ALS model. Nature. 429: 413-417.
Badie N, et al. (2009) A method to replicate the microstructure of heart tissue in vitro using DTMRI-based cell micropatterning. Ann Biomed Eng. 37: 2510-2521.
Bahr M, et al. (1991) In vitro myelination of regenerating adult rat retinal ganglion cell axons by Schwann cells. Glia. 4: 529-533.
Baker DC, et al. (2002) The origin and neuronal function of in vivo nonsynaptic glutamate. J Neurosci. 22: 9134-9141.
Bandi E, et al. (2008) Neural agrin controls maturation of the excitation-contraction coupling mechanism in human myotubes developing in vitro. Am J Physiol Cell Physiol. 294: C66-C73.
Bansal R, et al. (1992) Novel stage in the oligodendrocyte lineage defined by reactivity of progenitors with R-mAb prior to O1 antigalactocerebroside. J Neurosci Res. 32: 309-316.
Baraban SC, et al. (1997) Osmolarity modulates K+ channel function on rat hippocampal interneurons but not CA1 pyramidal neurons. J Physiol. 498: 679-689.
Barbulovic-Nad I, et al. (2008) Digital microfluidics for cell-based assays. Lab Chip. 8: 519-526.
Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.
Barone FC, et al. (1998) Ischemic preconditioning and brain tolerance: temporal histological and functional outcomes, protein synthesis requirement, and interleukin-1 receptor antagonist and early gene expression. Stroke. 29: 1937-1950; discussion 1950-1951.
Behar TN. (2001) Analysis of fractal dimension of O2A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid Al. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors-electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by muscle-derived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (O-2A) progenitor cells. Proc Natl Acad Sci U S A. 87: 6368-6372.
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silica simulation of synaptic processes. BMC Bioinformatics. 9 Suppl 4: S7.
Brand T, et al. (2000) EMBO Workshop Report: Molecular genetics of muscle development and neuromuscular diseases Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neural. 148: 475-494.
Bren-Mattison Y and Olwin BB. (2002) Sonic hedgehog inhibits the terminal differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neural. 159: 237-247.
Brito-Martins M, et al. (2008) beta(1)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.

(56) References Cited

OTHER PUBLICATIONS

Brumovsky P, et al. (2007) Expression of the vesicular glutamate transporters-1 and -2 in adult mouse dorsal root ganglia and spinal cord and their regulation by nerve injury. Neuroscience. 147: 469-490.
Bult CJ, et al. (1996) Complete genome sequence of the methanogenic archaeon, Methanococcus jannaschii. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.
Burdick JA and Vunjak-Novakovic G. (2008) Engineered microenvironments for controlled stem cell differentiation. Tissue Eng Part A. 15: 205-219.
Burgess C, et al. (2008) An endogenous glutamatergic drive onto somatic motoneurons contributes to the stereotypical pattern of muscle tone across the sleep-wake cycle. J Neurosci. 28: 4649-4660.
Butt HJ. (1996) Sensitive Method to Measure Changes in the Surface Stress of Solids. Journal of Colloid and Interface Science. 180: 251-260.
Buzanska L, et al. (2002) Human cord blood-derived cells attain neuronal and glial features in vitro. J Cell Sci. 115: 2131-2138.
Cai J, et al. (2007) Directed differentiation of human embryonic stem cells into functional hepatic cells. Hepatology. 45: 1229-1239.
Caiozzo VJ, at al. (1992) Response of slow and fast muscle to hypothyroidism: maximal shortening velocity and myosin isoforms. Am J Physiol. 263: C86-C94.
Cakir T, et al. (2007) Reconstruction and flux analysis of coupling between metabolic pathways of astrocytes and neurons: application to cerebral hypoxia. Theor Biol Med Model. 4: 48.
Campbell TJ and Williams KM. (2001) Therapeutic drug monitoring: antiarrhythmic drugs. Br J Clin Pharmacol. 52 Suppl 1: 21S-34S.
Camu W and Henderson CE. (1992) Purification of embryonic rat motoneurons by panning on a monoclonal antibody to the low-affinity NGF receptor. J Neurosci Methods. 44: 59-70.
Camu W and Henderson CE. (1994) Rapid purification of embryonic rat motoneurons: an in vitro model for studying MND/ALS pathogenesis. J Neurol Sci. 124 Suppl: 73-74.
Cannon JG. (1998) Intrinsic and extrinsic factors in muscle aging Ann N Y Acad Sci. 854: 72-77.
Caratsch CG, et al. (1994) Interferon-alpha, beta and tumor necrosis factor-alpha enhance the frequency of miniature end-plate potentials at rat neuromuscular junction. Neurosci Lett. 166: 97-100.
Carlsson L. (2006) In vitro and in vivo models for testing arrhythmogenesis in drugs. J Intern Med. 259: 70-80.
Carpenedo RL, et al. (2007) Rotary suspension culture enhances the efficiency, yield, and homogeneity of embryoid body differentiation. Stem Cells. 25: 2224-2234.
Carr PA, et al. (1989) Parvalbumin is highly colocalized with calbindin D28k and rarely with calcitonin gene-related peptide in dorsal root ganglia neurons of rat. Brain Res. 497: 163-170.
Carrasco DI and English AW. Neurotrophin 4/5 is required for the normal development of the slow muscle fiber phenotype in the rat soleus. J Exp Biol. 206: 2191-2200.
Caspi O, et al. (2009) In vitro electrophysiological drug testing using human embryonic stem cell derived cardiomyocytes. Stem Cells Dev. 18: 161-172.
Catoire H, et al. (2008) Sirtuin inhibition protects from the polyalanine muscular dystrophy protein PABPN1. Hum Mol Genet. 17: 2108-2117.
Cerignoli F, et al. (2012) High throughput measurement of $Ca^{2+}$ dynamics for drug risk assessment in human stem cell-derived cardiomyocytes by kinetic image cytometry. J Pharmacol Toxicol Methods. 66: 246-256.
Chambers SM, et al. (2009) Highly efficient neural conversion of human ES and iPS cells by dual inhibition of SMAD signaling. Nat Biotechnol. 27: 275-280.
Chandran S, et al. (1998) Regional potential for oligodendrocyte generation in the rodent embryonic spinal cord following exposure to EGF and FGF-2. Glia. 24: 382-389.
Chang JC, et al. (2001) Modulation of neural network activity by patterning. Biosens Bioelectron. 16: 527-533.
Charpentier A, et al. (1993) RRR-alpha-tocopheryl succinate inhibits proliferation and enhances secretion of transforming growth factor-beta (TGF-beta) by human breast cancer cells. Nutr Cancer. 19: 225-239.
Chaudhary KW, et al. (2006) Embryonic stem cells in predictive cardiotoxicity: laser capture microscopy enables assay development. Toxicol Sci. 90: 149-158.
Chaves M, et al. (2005) Robustness and fragility of Boolean models for genetic regulatory networks. J Theor Biol. 235: 431-449.
Chaves M, et al. (2006) Methods of robustness analysis for Boolean models of gene control networks. Syst Biol (Stevenage). 153: 154-167.
Chen CS, et al. (1997) Geometric control of cell life and death. Science. 276: 1425-1428.
Chen EW, et al. (1995) Target regulation of a motor neuron-specific epitope. J Neurosci. 15: 1555-1566.
Chen J and von Bartheld CS. (2004) Role of exogenous and endogenous trophic factors in the regulation of extraocular muscle strength during development.Invest Ophthalmol Vis Sci. 45: 3538-3545.
Chen QS, et al. (2000) Impairment of hippocampal long-term potentiation by Alzheimer amyloid beta-peptides. J Neurosci Res. 60: 65-72.
Chen X, et al. (2005) Dedifferentiation of adult human myoblasts induced by ciliary neurotrophic factor in vitro. Moll Biol Cell. 16: 3140-3151.
Chen XF, et al. (2008) Dynamic simulation of the effect of calcium-release activated calcium channel on cytoplasmic Ca2+ oscillation. Biophys Chem. 136: 87-95.
Chen XP, (2003) [Exogenous rhCNTF inhibits myoblast differentiation of skeletal muscle of adult human in vitro]. Sheng Li Xue Bao. 55: 464-468.
Chiu AY, et al. (1993) A motor neuron-specific epitope and the low-affinity nerve growth factor receptor display reciprocal patterns of expression during development, axotomy, and regeneration. J Comp Neurol. 328: 351-363.
Choi-Lundberg DL and Bohn MC. (1995) Ontogeny and distribution of glial cell line-derived neurotrophic factor (GDNF) mRNA in rat. Brain Res Dev Brain Res. 85: 80-88.
Choudhury A, et al. (2007) A piezoresistive microcantilever array for surface stress measurement: curvature model and fabrication. J Micromech Microeng. 17: 2065-2076.
Chow I and Poo MM. (1985) Release of acetylcholine from embryonic neurons upon contact with muscle cell. J Neurosci. 5: 1076-1082.
Christ B and Brand-Seberi B. (2002) Limb muscle development. Int J Dev Biol. 46: 905-914.
Cizkova D, et al. (2007) Functional recovery in rats with ischemic paraplegia after spinal grafting of human spinal stem cells. Neuroscience. 147: 546-560.
Clegg CH, et al. (1987) Growth factor control of skeletal muscle differentiation: commitment to terminal differentiation occurs in G1 phase and is repressed by fibroblast growth factor. J Cell Biol. 105: 949-956.
Clements JD, et al. (1992) The time course of glutamate in the synaptic cleft. Science. 258: 1498-1501.
Coggan JS, et al. (2005) Evidence for ectopic neurotransmission at a neuronal synapse. Science. 309: 446-451.
Cohen RI and Almazan G. (1993) Norepinephrine-stimulated PI hydrolysis in oligodendrocytes is mediated by alpha 1A-adrenoceptors. Neuroreport. 4: 1115-1118.
Cohen-Cory S. (2002) The developing synapse: construction and modulation of synaptic structures and circuits. Science. 298: 770-776.

(56) References Cited

OTHER PUBLICATIONS

Collins CA and Morgan JE. (2003) Duchenne's muscular dystrophy: animal models used to investigate pathogenesis and develop therapeutic strategies. Int J Exp Pathol. 84: 165-172.

Colomar A and Robitaille R. (2004) Glial modulation of synaptic transmission at the neuromuscular junction. Glia. 47: 284-289.

Cooper A, et al. (1976) The growth of mouse neuroblastoma cells in controlled orientations on thin films of silicon monoxide. Exp Cell Res. 103: 435-439.

Corey JM, et al. (1991) Compliance of hippocampal neurons to patterned substrate networks. J Neurosci Res. 30: 300-307.

Corey JM, et al. (1996) Micrometer resolution silane-based patterning of hippocampal neurons: critical variables in photoresist and laser ablation processes for substrate fabrication. IEEE Trans Biomed Eng. 43: 944-955.

Corey JM, et al. (1997) Differentiated B104 neuroblastoma cells are a high-resolution assay for micropatterned substrates. J Neurosci Methods. 75: 91-97.

Cortassa S, et al. (2003) an integrated model of cardiac mitochondrial energy metabolism and calcium dynamics. Biophys J. 84: 2734-2755.

Cossu G, et al. (1996) How is myogenesis initiated in the embryo? Trends Genet. 12: 218-223.

Courdier-Fruh I, et al. (2002) Glucocorticoid-mediated regulation of utrophin levels in human muscle fibers. Neuromuscul Disord. 12(Suppl 1): S95-S104.

Cross-Doersen D and Isfort RJ. (2003) A novel cell-based system for evaluating skeletal muscle cell hypertrophy-inducing agents. In Vitro Cell Dev Biol Animal. 39: 407-412.

Cukierman E, et al. (2002) Cell interactions with three-dimensional matrices. Curr Opin Cell Biol. 14: 633-639.

Cunningham JJ and Roussel MF. (2001) Cyclin-dependent kinase inhibitors in the development of the central nervous system. Cell Growth Differ. 12: 387-396.

Cuppini R, et al. (2001) Alpha-tocopherol controls cell proliferation in the adult rat dentate gyrus. Neurosci Lett. 303: 198-200.

Currie PD and Ingham PW. (1996) Induction of a specific muscle cell type by a hedgehog-like protein in zebrafish. Nature. 382: 452-455.

Curtis R, et al. (1988) Development of macroglial cells in rat cerebellum. I. Use of antibodies to follow early in vivo development and migration of oligodendrocytes. J Neurocytol. 17: 43-54.

Cysyk J and Tung L. (2008) Electric field perturbations of spiral waves attached to millimeter-size obstacles. Biophys J. 94: 1533-1541.

Dakhel Y and Jamali F. (2006) Erythromycin potentiates PR interval prolonging effect of verapamil in the rat: a pharmacodynamic drug interaction. Toxicol Appl Pharmacol. 214: 24-29.

Daniels MP, et al. (2000) Rodent nerve-muscle cell culture system for studies of neuromuscular junction development: refinements and applications. Microsc Res Tech. 49: 26-37.

Daniels MP. (1990) Localization of actin, beta-spectrin, 43×10(3) Mr and 58×10(3) Mr proteins to receptor-enriched domains of newly formed acetylcholine receptor aggregates in isolated myotube membranes. J Cell Sci. 97(Pt 4): 615-626.

Daniels MP. (1997) Intercellular communication that mediates formation of the neuromuscular junction. Mol Neurobiol. 14: 143-170.

Das M, et al. (2003) Electrophysiological and morphological characterization of rat embryonic motoneurons in a defined system. Biotechnol Prog. 19: 1756-1761.

Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.

Das M, et al. (2006) A defined system to allow skeletal muscle differentiation and subsequent integration with silicon microstructures. Biomaterials. 27: 4374-4380.

Das M, et al. (2007a) Auto-catalytic ceria nanoparticles offer neuroprotection to adult rat spinal cord neurons. Biomaterials. 28: 1918-1925.

Das M, et al. (2007b) Differentiation of skeletal muscle and integration of myotubes with silicon microstructures using serum-free medium and a synthetic silane substrate. Nat Protoc. 2: 1795-1801.

Das M, et al. (2007c) Embryonic motoneuron-skeletal muscle co-culture in a defined system. Neuroscience. 146: 481-488.

Das M, et al. (2008) Temporal neurotransmitter conditioning restores the functional activity of adult spinal cord neurons in long-term culture. Exp Neurol. 209: 171-180.

Das M, et al. (2009a) Developing a novel serum-free cell culture model of skeletal muscle differentiation by systematically studying the role of different growth factors in myotube formation. In Vitro Cell Dev Biol Anim. 45: 378-387.

Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.

Das M, et al. (2010) A defined long-term in vitro tissue engineered model of neuromuscular junctions. Biomaterials. 31: 4880-4888.

Datar R, et al. (2009) Cantilever Sensors: Nanomechanical Tools for Diagnostics. MRS Bulletin. 34: 449-454.

David JA and Pitman RM. (1982) The effects of axotomy upon the extrasynaptic acetylcholine sensitivity of an identified motoneurone in the cockroach Periplaneta americana. J Exp Biol. 98: 329-341.

Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.

De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.

De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.

de Lange P, et al. (2006) Sequential changes in the signal transduction responses of skeletal muscle following food deprivation. FASEB J. 20: 2579-2581.

de Wilde J, et al. (2008) Short-term high fat-feeding results in morphological and metabolic adaptations in the skeletal muscle of C57BL/6J mice. Physiol Genomics. 32: 360-369.

Dell'Era P, et al. (2003) Fibroblast growth factor receptor-1 is essential for in vitro cardiomyocyte development. Circ Res. 93: 414-420.

Denning C and Anderson D. (2008) Cardiomyocytes from human embryonic stem cells as predictors of cardiotoxicity. Drug Discovery Today: Therapeutic Strategies. 5: 223-232.

Dennis RG and Kosnik IPE. (2000) Excitability and isometric contractile properties of mammalian skeletal muscle constructs engineered in vitro. In Vitro Cell Dev Biol Anim. 36: 327-335.

Dennis RG, et al. (2001) Excitability and contractility of skeletal muscle engineered from primary cultures and cell lines. Am J Physiol Cell Physiol. 280: C288-C295.

Denyer MCT, et al. (1998) Preliminary study on the suitability of a pharmacological bio-assay based on cardiac myocytes cultured over microfabricated microelectrode arrays. Med Biol Eng Comput. 36: 638-644.

Descarries L, et al. (1997) Diffuse transmission by acetylcholine in the CNS. Prog Neurobiol. 53: 603-625.

Dhavan R and Tsai L. (2001) A decade of CDK5. Nat Rev Mol Cell Biol. 2: 749-759.

Dhir V, et al. (2009) Patterning of diverse mammalian cell types in serum free medium with photoablation. Biotechnol Prog. 25: 594-603.

Di Giovanni S, et al. (2005) Cell cycle inhibition provides neuroprotection and reduces glial proliferation and scar formation after traumatic brain injury. Proc Natl Acad Sci U S A. 102: 8333-8338.

Dimitrova DS and Gilbert DM. (2000) Temporally coordinated assembly and disassembly of replication factories in the absence of DNA synthesis. Nat Cell Biol. 2: 686-694.

(56) References Cited

OTHER PUBLICATIONS

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacology. 24: 254-264.

Duport S, et al. (1999) A metallic multisite recording system designed for continuous long-term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes in vitro. Differentiation. 65 : 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microelectrode arrays. In: Taketani M BM, editor. Advances in netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/Akt pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression of homeobox gene Islet-1. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by self-assembly processes. Bioorg Med Chem. 7: 75-81.

Figenschou A, et al. (1996) Cholinergic modulation of the action potential in rat hippocampal neurons. Eur J Neurosci. 8: 211-219.

Fink CC, et al. (1999) Determination of time-dependent inositol-1,4,5-trisphosphate concentrations during calcium release in a smooth muscle cell. Biophys J. 77: 617-628.

Fischbach GD and Cohen SA. (1973) The distribution of acetylcholine sensitivity over uninnervated and innervated muscle fibers grown in cell culture. Dev Biol. 31: 147-162.

Fischbach GD. (1972) Synapse formation between dissociated nerve and muscle cells in low density cell cultures. Dev Biol. 28: 407-429.

Fisher OZ, et al. (2010) Bioinspired materials for controlling stem cell fate. Acc Chem Res. 43: 419-428.

Silverberg, (2002) The cerebrospinal fluid production rate is reduced in dementia of the Alzheimer's type. Neurology. 58: 1866; author reply 1866.

Flucher BE, et al. (1990) Localization of the alpha 1 and alpha 2 subunits of the dihydropyridine receptor and ankyrin in skeletal muscle triads. Neuron. 5: 339-351.

Flucher BE, et al. (1991) Biogenesis of transverse tubules in skeletal muscle in vitro. Dev Biol. 145: 77-90.

Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.

Flucher BE, et al. (1994) Molecular organization of transverse tubule/sarcoplasmic reticulum junctions during development of excitation-contraction coupling in skeletal muscle. Mol Biol Cell. 5: 1105-1118.

Forry SP, et al. (2006) Facilitating the culture of mammalian nerve cells with polyelectrolyte multilayers. Langmuir. 22: 5770-5775.

Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.

Fowler VM, et al. (1993) Tropomodulin is associated with the free (pointed) ends of the thin filaments in rat skeletal muscle. J Cell Biol. 120: 411-420.

Fox MA, et al. (2007) Distinct target-derived signals organize formation, maturation, and maintenance of motor nerve terminals. Cell. 129: 179-193.

Francis PT. (2008) Glutamatergic approaches to the treatment of cognitive and behavioural symptoms of Alzheimer's disease. Neurodegener Dis. 5: 241-243.

Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.

Franzini-Armstrong C and Protasi F. (1997) Ryanodine receptors of striated muscles: a complex channel capable of multiple interactions. Physiol Rev. 77: 699-729.

Friedman B, et al. (1995) BDNF and NT-4/5 exert neurotrophic influences on injured adult spinal motor neurons. J Neurosci. 15: 1044-1056.

Fu X, et al. (1995) Acidic fibroblast growth factor reduces rat skeletal muscle damage caused by ischemia and reperfusion. Chin Med J (Engl). 108: 209-214.

(56) References Cited

OTHER PUBLICATIONS

Fuentes-Medel Y, et al. (2012) Integration of a retrograde signal during synapse formation by glia-secreted TGF-β ligand. Curr Biol. 22: 1831-1838.
Funakoshi H, et al. (1995) Muscle-derived neurotrophin-4 as an activity-dependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175: 50-57.
Galizia CG and Menzel R. (2000) Probing the olfactory code. Nat Neurosci. 3: 853-854.
Gao BX and Ziskind-Conhaim L. (1995) Development of glycine- and GABA-gated currents in rat spinal motoneurons. J Neurophysiol. 74: 113-121.
Gao BX and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69: 4027-4037.
Gaud A, et al. (2004) Prednisone reduces muscle degeneration in dystrophin-deficient Caenorhabditis elegans. Neuromuscul Disord. 14: 365-370.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kip1) and p21(CIP1) accumulation and G1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass L and Kauffman SA. (1973) The logical analysis of continuous, non-linear biochemical control networks. J Theor Biol. 39: 103-129.
Glass L. (1975) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neural. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mal Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gazes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83: 2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374: 1745-1753.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNP1. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.
Gureviciene I, et al. (2004) Normal induction but accelerated decay of LTP in APP+PS1 transgenic mice. Neurobiol Dis. 15: 188-195.
Haas HL and Selbach O. (2000) Functions of neuronal adenosine receptors. Naunyn Schmiedebergs Arch Pharmacol. 362: 375-381.

(56) References Cited

OTHER PUBLICATIONS

Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly(ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U S A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hermann M, et al. (2006) Exposure of atorvastatin is unchanged but lactone and acid metabolites are increased several-fold in patients with atorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. (1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.

Hoffman EP and Escolar D. (2006) Translating mighty mice into neuromuscular therapeutics: is bigger muscle better? Am J Pathol. 168: 1775-1778.
Hofmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffman P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-294.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRIaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alpha1A-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-on-chips. Lab Chip. 12: 2156-2164.
Hui EE and Bhatia SN. (2007) Microscale control of cell contact and spacing via three-component surface patterning. Langmuir. 23: 4103-4107.
Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Brn-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein in neonatal rat cultured cardiomyocytes: involvement of mitogen-activated protein kinases and effects of angiotensin II-receptor antagonist. J Am Coll Cardiol. 44: 914-922.
Iravanian S, et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20: 2333-2342.

(56) References Cited

OTHER PUBLICATIONS

Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci, 20: 2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. FASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.
Johnson TE, et al. (2005) Statins and PPARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, Impedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11: 1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-201.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci U S A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001) Acute toxicity screening of novel AChE inhibitors using neuronal networks on microelectrode arrays. Neurotoxicology. 22: 3-12.
Keefer EW, et al. (2001) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. J Neurosci Res. 58: 765-778.
Khorchid A, et al. (2002) Developmental regulation of alpha 1A-adrenoceptor function in rat brain oligodendrocyte cultures. Neuropharmacology. 42: 685-696.
Kidambi S, et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expiries. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim J, et al. (2002) Dopamine neurons derived from embryonic stem cells function in an animal model of Parkinson's disease. Nature. 418: 50-56.
Kim K, et al. (2011) Calibrated microthropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
King T, et al. (2000) Piezoactuators for 'real-world' applications—Can they deliver sufficient displacement? Power Engineering. 14: 105-110.
Kingshott P and Griesser HJ. (1999) Surfaces that resist bioadhesion. Current Opinion in Solid State and Materials Science. 4: 403-412.
Kirazov E, et al. (2008) Amyloid beta peptides exhibit functional neurotoxicity to cortical network cultures. Compt Rend Acad Bulg Sci. 61: 905-910.
Kita-Matsuo H, et al. (2009) Lentiviral vectors and protocols for creation of stable hESC lines for fluorescent tracking and drug resistance selection of cardiomyocytes. PLoS One. 4: e5046.
Kleber AG and Rudy Y. (2004) Basic mechanisms of cardiac impulse propagation and associated arrhythmias. Physiol Rev. 84: 431-488.
Klein C, et al. (2002) Zinc inhibition of cAMP signaling. J Biol Chem. 277: 11859-11865.
Kleinfeld D, et al. (1988) Controlled outgrowth of dissociated neurons on patterned substrates. J Neurosci. 8: 4098-4120.
Knobloch M and Mansuy IM. (2008) Dendritic spine loss and synaptic alterations in Alzheimer's disease. Mol Neurobiol. 37: 73-82.

(56) References Cited

OTHER PUBLICATIONS

Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.
Kobayashi T, et al. (1987) Human muscle cultured in monolayer and cocultured with fetal rat spinal cord: importance of dorsal root ganglia for achieving successful functional innervation. J Neurosci. 7: 3131-3141.
Koike T, et al. (2008) Axon & dendrite degeneration: its mechanisms and protective experimental paradigms. Neurochem Int. 52: 751-760.
Koirala S, et al. (2003) Roles of glial cells in the formation, function, and maintenance of the neuromuscular junction. J Neurocytol. 32: 987-1002.
Koleva M, et al. (2005) Pleiotropic effects of sonic hedgehog on muscle satellite cells. Cell Mol Life Sci. 62: 1863-1870.
Koliatsos VE, et al. (2008) Human stem cell grafts as therapies for motor neuron disease. Expert Opin Biol Ther. 8: 137-141.
Kontrogianni-Konstantopoulos A, et al. (2009) Muscle giants: molecular scaffolds in sarcomerogenesis. Physiol Rev. 89: 1217-1267.
Kornblum HI, et al. (1999) Multiple trophic actions of heparin-binding epidermal growth factor (HB-EGF) in the central nervous system. Eur J Neurosci. 11: 3236-3246.
Kucera J and Dorovini-Zis K. (1979). Types of human intrafusal muscle fibers. Muscle Nerve. 2: 437-451.
Kucera J and Walro J. (1992) Axotomy induces fusimotor-free muscle spindles in neonatal rats. Neurosci Lett. 136: 216-218.
Kucera J, et al. (1989) Role of nerve and muscle factors in the development of rat muscle spindles. Am J Anat. 186: 144-160.
Kucera J. (1982a) One-bag-fiber muscle spindles in tenuissimus muscles of the cat. Histochemistry and Cell Biology. 76: 315-328.
Kucera, J. (1982b). The topography of long nuclear chain intrafusal fibers in the cat muscle spindle. Histochemistry. 74: 183-197.
Kucera, J. (1983). Multiple-bag-fiber muscle spindles in tenuissimus muscles of the cat. Histochemistry. 79: 457-476.
Kudla AJ, et al. (1995) A requirement for fibroblast growth factor in regulation of skeletal muscle growth and differentiation cannot be replaced by activation of platelet-derived growth factor signaling pathways. Mol Cell Biol. 15: 3238-3246.
Kuhl U, et al. (1982) Synthesis of type IV collagen and laminin in cultures of skeletal muscle cells and their assembly on the surface of myotubes. Dev Biol. 93: 344-354.
Kuhl U, et al. (1986) Role of laminin and fibronectin in selecting myogenic versus fibrogenic cells from skeletal muscle cells in vitro. Dev Biol. 117: 628-635.
Kurek JB, et al. (1996) Leukemia inhibitory factor and interleukin-6 are produced by diseased and regenerating skeletal muscle. Muscle Nerve. 19: 1291-1301.
Lacor PN, et al. (2007) Abeta oligomer-induced aberrations in synapse composition, shape, and density provide a molecular basis for loss of connectivity in Alzheimer's disease. J Neurosci. 27: 796-807.
Lacor PN. (2007) Advances on the understanding of the origins of synaptic pathology in AD. Curr Genomics. 8: 486-508.
Laflamme MA, et al. (2007) Cardiomyocytes derived from human embryonic stem cells in pro-survival factors enhance function of infarcted rat hearts. Nat Biotechnol. 25: 1015-1024.
Lamb TM, et al. (1993) Neural induction by the secreted polypeptide noggin. Science. 262: 713-718.
Lambert MP, et al. (1998) Diffusible, nonfibrillar ligands derived from Abeta1-42 are potent central nervous system neurotoxins. Proc Natl Acad Sci U S A. 95: 6448-6453.
Lambeth MJ and Kushmerick MJ. (2002) A computational model for glycogenolysis in skeletal muscle. Ann Biomed Eng. 30: 808-827.
Lambrechts D, et al. (2003) VEGF is a modifier of amyotrophic lateral sclerosis in mice and humans and protects motoneurons against ischemic death. Nat Genet. 34: 383-394.
Langen RC, et al. (2003) Enhanced myogenic differentiation by extracellular matrix is regulated at the early stages of myogenesis. In Vitro Cell Dev Biol Anim. 39: 163-169.
Langer R and Vacanti JP. (1993) Tissue engineering. Science. 260: 920-926.
Larkin LM, et al. (2006) Functional evaluation of nerve-skeletal muscle constructs engineered in vitro. In Vitro Cell Dev Biol Anim. 42: 75-82.
Larsson L and Ansved T. (1995) Effects of ageing on the motor unit. Prog Neurobiol. 45: 397-415.
Lasser KE, et al. (2002) Timing of new black box warnings and withdrawals for prescription medications. JAMA. 287: 2215-2220.
Lawrence CL, et al. (2005) Nonclinical proarrhythmia models: predicting Torsades de Pointes. J Pharmacol Toxicol Methods. 52: 46-59.
Lawrence CL, et al. (2006) A rabbit Langendorff heart proarrhythmia model: predictive value for clinical identification of Torsades de Pointes. Br J Pharmacol. 149: 845-860.
Le Douarin NM and Dupin E. (2003) Multipotentiality of the neural crest. Curr Opin Genet Dev. 13: 529-536.
Lee A. (2005) Isolation of neural stem cells from the postnatal cerebellum. Nat Neurosci. 8: 723-729.
Lee EW, et al. (2003) Neuropeptide Y induces ischemic angiogenesis and restores function of ischemic skeletal muscles. J Clin Invest. 111: 1853-1862.
Lee G, et al. (2007) Isolation and directed differentiation of neural crest stem cells derived from human embryonic stem cells. Nat Biotechnol. 25: 1468-1475.
Lee G, et al. (2010) Derivation of neural crest cells from human pluripotent stem cells. Nat Protoc. 5: 688-701.
Lee HY, et al. (2004) Instructive role of Wnt/beta-catenin in sensory fate specification in neural crest stem cells. Science. 303: 1020-1023.
Lee MJ, et al. (2003) Hereditary sensory neuropathy is caused by a mutation in the delta subunit of the cytosolic chaperonin-containing t-complex peptide-1 (Cct4) gene. Hum Mol Genet. 12: 1917-1925.
Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.
Lescaudron L, et al. (1999) Blood borne macrophages are essential for the triggering of muscle regeneration following muscle transplant. Neuromuscul Disord. 9: 72-80.
Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5. Proc Natl Acad Sci U S A. 98: 12742-12747.
Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4: e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. Curr Neurovasc Res. 3: 281-288.
Lin JW, et al. (2008) Region [corrected] of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.

(56) References Cited

OTHER PUBLICATIONS

Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations in DRG neurons: relation to neuropathic pain. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci U S A. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci U S A. 102: 701-706.
Lochter AJ, et al. (1995) Control of neuronal morphology in vitro: interplay between adhesive substrate forces and molecular instruction. J Neurosci Res. 42: 145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Love S. (2003) Neuronal expression of cell cycle-related proteins after brain ischaemia in man. Neurosci Lett. 353: 29-32.
Lu B, et al. (1996) Expression of synapsin I correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit 1C.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Int J Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-502.
Malerba A, et al. (2009) Selection of multipotent cells and enhanced muscle reconstruction by myogenic macrophage-secreted factors. Exp Cell Res. 315: 915-927.
Malm C, et al. (2004) Leukocytes, cytokines, growth factors and hormones in human skeletal muscle and blood after uphill or downhill running. J Physiol. 556: 983-1000.

Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.
Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. ASAIO J. 38: M243-M247.
Matthews PB. (1964) Muscle spindles and their motor control. Physiol Rev. 44: 219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.
Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.
Maynard EM. (2001) Visual prostheses. Annu Rev Biomed Eng. 3: 145-168.
McAuliffe GJ, et al. (2008) Development of a gastrointestinal tract microscale cell culture analog to predict drug transport. Mol Cell Biomech. 5: 119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12: 1438-1452.
Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Acc Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci U S A. 98: 1235-1240.
Mendelsohn JD, et al. (2003) Rational design of cytophilic and cytophobic polyelectrolyte multilayer thin films. Biomacromolecules. 2003 4: 96-106.
Menendez L, et al. (2011) Wnt signaling and a Smad pathway blockade direct the differentiation of human pluripotent stem cells to multipotent neural crest cells. Proc Natl Acad Sci U S A. 108: 19240-19245.
Menn B, et al. (2010) Delayed treatment with systemic (S)-roscovitine provides neuroprotection and inhibits in vivo CDK5 activity increase in animal stroke models. PLoS One. 5: e12117.

(56) References Cited

OTHER PUBLICATIONS

Metzger SW, et al. (1999) Development and characterization of surface chemistries for microfabricated biosensors. J of Vacuum Sci & Tech a—Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural origins for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci U S A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.
Mohan DK, et al. (2006) Toxin detection based on action potential shape analysis using a realistic mathematical model of differentiated NG108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2005) Biosurface Engineering. Encyclopedia of Medical Devices and Instrumentation. J.G. Webster. New York, John Wiley & Sons, Inc.
Molnar P, et al. (2007) Photolithographic Patterning of C2C12 Myotubes using Vitronectin as Growth Substrate in Serum-Free Medium. Biotechnol Prog. 23: 265-268.
Molnar P, et al. (2007b) Synaptic connectivity in engineered neuronal networks. Methods Mol Biol. 403: 165-173.
Molnar P, et al. (2007c) Modeling of action potential generation in NG108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68: 1331-1342.
Monaco EA 3rd. (2004) Recent evidence regarding a role for CdkS dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogenic differentiation. Development. 111: 741-748.
Morefield SI, et al. (2000) Drug evaluations using neuronal networks cultured on microelectrode arrays. Biosens Bioelectron. 15: 383-396.
Morganroth J and Gussak I. (2004) Cardiac Safety of Noncardiac Drugs: Practical Guidelines for Clinical Research and Drug Development. New York, Humana Press.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-1 mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIA1 Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate $CO_2/H+$-sensitive neurons in rat brain stem slices. J Appl Physiol. 95: 910-921.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Müller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.
Muraki K, et al. (1994) Effects of noradrenaline on membrane currents and action potential shape in smooth muscle cells from guinea-pig ureter. J Physiol. 481: 617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan To Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2006) Evidence for multiple mechanisms in human ventricular fibrillation. Circulation. 114: 536-542.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32: 4267-4274.
Natarajan A, et al. (2013) Engineered In Vitro Feed-Forward Networks. J Biotechnol Biomater. 3: 153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.

(56) References Cited

OTHER PUBLICATIONS

Nelson CM and Bisell MJ. (2006) Of extracellular matrix, scaffolds, and signaling: tissue architecture regulates development, homeostasis, and cancer. Annu Rev Cell Dev Biol. 22: 287-309.

Nelson PG, et al. (1993) Synapse elimination from the mouse neuromuscular junction in vitro: a non-Hebbian activity-dependent process. J Neurobiol. 24: 1517-1530.

Nelson PG. (1975) Nerve and muscle cells in culture. Physiol Rev. 55: 1-61.

Nerbonne JM and Kass RS. (2005) Molecular physiology of cardiac repolarization. Physiol Rev. 85: 1205-1253.

Nguemo F, et al. (2012) In vitro model for assessing arrhythmogenic properties of drugs based on high-resolution impedance measurements. Cell Physiol Biochem. 29: 819-832.

Nguyen L, et al. (2006) The Yin and Yang of cell cycle progression and differentiation in the oligodendroglial lineage. Ment Retard Dev Disabil Res Rev. 12: 85-96.

Nicolelis MAL and Ribeiro S. (2002) Multielectrode recordings: the next steps. Curr Opin Neurobiol. 12: 602-606.

Nimmrich V, et al. (2008) Amyloid beta oligomers (A beta(1-42) globulomer) suppress spontaneous synaptic activity by inhibition of P/Q-type calcium currents. J Neurosci. 28: 788-797.

Nishikawa J, et al. (2005) Increase of Cardiotrophin-1 immunoreactivity in regenerating and overloaded but not denervated muscles of rats. Neuropathology. 25: 54-65.

Nishimaru H, et al. (2005) Mammalian motor neurons corelease glutamate and acetylcholine at central synapses. Proc Natl Acad Sci U S A. 102: 5245-5249.

Nistor GI, et al. (2005) Human embryonic stem cells differentiate into oligodendrocytes in high purity and myelinate after spinal cord transplantation. Glia. 49: 385-396.

Noble D. (2004) Modeling the heart. Physiology (Bethesda). 19: 191-197.

Noll E and Miller RH. (1993) Oligodendrocyte precursors originate at the ventral ventricular zone dorsal to the ventral midline region in the embryonic rat spinal cord. Development. 118: 563-573.

Normann RA, et al. (1999) A neural interface for a cortical vision prosthesis. Vision Res. 39: 2577-2587.

Norris W, et al. (2000) Slow muscle induction by Hedgehog signalling in vitro. J Cell Sci. 113: 2695-2703.

Nyitrai G, et al. (2006) Extracellular level of GABA and Glu: in vivo microdialysis-HPLC measurements. Curr Top Med Chem. 6: 935-940.

Oakley RA, et al. (1997) Neurotrophin-3 promotes the differentiation of muscle spindle afferents in the absence of peripheral targets. J Neurosci. 17: 4262-4274.

O'Connor SM, et al. (2000) Immobilization of neural cells in three-dimensional matrices for biosensor applications. Biosens Bioelectron. 14: 871-881.

Offenhausser A and Knoll W. (2001) Cell-transistor hybrid systems and their potential applications. Trends Biotechnol. 19: 62-66.

Offenhausser A, et al. (1997) Field-effect transistor array for monitoring electrical activity from mammalian neurons in culture. Biosensors and Bioelectronics. 12: 819-826.

Oh TI, et al. (2007) Real-time fluorescence detection of multiple microscale cell culture analog devices in situ. Cytometry A. 71: 857-865.

Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.

Olson E. (1992a) Activation of muscle-specific transcription by myogenic helix-loop-helix proteins. Symp Soc Exp Biol. 46: 331-341.

Olson EN and Perry WM. (1992b) MyoD and the paradoxes of myogenesis. Curr Biol. 2: 35-37.

Olson EN and Williams RS. (2000) Calcineurin Signaling and Muscle Remodeling. Cell. 101: 689-692.

Olson EN. (1992c) Interplay between proliferation and differentiation within the myogenic lineage. Dev Biol. 154: 261-272.

Olwin BB and Rapraeger A. (1992) Repression of myogenic differentiation by aFGF, bFGF, and K-FGF is dependent on cellular heparan sulfate. J Cell Biol. 118: 631-639.

Oppenheim RW, et al. (1991) Control of embryonic motoneuron survival in vivo by ciliary neurotrophic factor. Science. 251: 1616-1618.

Oppenheim RW, et al. (2001) Cardiotrophin-1, a muscle-derived cytokine, is required for the survival of subpopulations of developing motoneurons. J Neurosci. 21: 1283-1291.

Orentas DM and Miller RH. (1998) Regulation of oligodendrocyte development. Mol Neurobiol. 18: 247-259.

Orlov SN and Hamet P. (2006) Intracellular monovalent ions as second messengers. J Membr Biol. 210: 161-172.

Ostuni E, et al. (2000) Patterning mammalian cells using elastomeric membranes. Langmuir. 16: 7811-7819.

Oumata N, et al. (2008) Roscovitine-derived, dual-specificity inhibitors of cyclin-dependent kinases and casein kinases 1. J Med Chem. 51: 5229-5242.

Padmanabhan J, et al. (1999) Role of cell cycle regulatory proteins in cerebellar granule neuron apoptosis. J Neurosci. 19: 8747-8756.

Pagan SM, et al. (1996) Surgical removal of limb bud Sonic hedgehog results in posterior skeletal defects. Dev Biol. 180: 35-40.

Pancrazio JJ, et al. (1998) Portable cell-based biosensor system for toxin detection. Sensors and Actuators B Chem. 53: 179-185.

Park J, et al. (2005) Real-time measurement of the contractile forces of self-organized cardiomyocytes on hybrid biopolymer microcantilevers. Anal Chem. 77: 6571-6580.

Parker KK, et al. (2008) Myofibrillar architecture in engineered cardiac myocytes. Circ Res. 103: 340-342.

Parng C, et al. (2002) Zebrafish: A Preclinical Model for Drug Screening. Assay Drug Dev Technol. 1:41-48.

Parviz M and Gross GW. (2007) Quantification of zinc toxicity using neuronal networks on microelectrode arrays. Neurotoxicology. 28: 520-531.

Paspalas CD and Papadopoulos GC. (1996) Ultrastructural relationships between noradrenergic nerve fibers and non-neuronal elements in the rat cerebral cortex. Glia. 17: 133-146.

Payne ET, et al. (2006) Nutritional therapy improves function and complements corticosteroid intervention in mdx mice. Muscle Nerve. 33: 66-77.

Peng HB, et al. (2003) Differential effects of neurotrophins and schwann cell-derived signals on neuronal survival/growth and synaptogenesis. J Neurosci. 23: 5050-5060.

Peroulakis ME and Forger NG. (2000) Ciliary neurotrophic factor increases muscle fiber number in the developing levator ani muscle of female rats. Neurosci Lett. 296: 73-76.

Perrier AL, et al. (2004) Derivation of midbrain dopamine neurons from human embryonic stem cells. Proc Natl Acad Sci U S A. 101: 12543-12548.

Peters A. (1964) Observations on the Connexions Between Myelin Sheaths and Glial Cells in the Optic Nerves of Young Rats. J Anat. 98: 125-134.

Peterson CA, et al. (1999) Effects of moisture on Fowler—Nordheim characterization of thin silicon-oxide films. J Vac Science Technol A. 17: 2753-2758.

Pette D and Staron S. (2001) Transitions of muscle fiber phenotypic profiles. Histochem and Cell Biol. 115: 359-372.

Pette D, et al. (2002) Partial fast-to-slow conversion of regenerating rat fast-twithc muscle by chronic low frequency stimulation. J Muscle Res Cell Motil. 3: 215-221.

Pfeiffer SE, et al. (1993) The oligodendrocyte and its many cellular processes. Trends Cell Biol. 3: 191-197.

Pfrieger FW and Barres BA. (1997) Synaptic efficacy enhanced by glial cells in vitro. Science. 277: 1684-1687.

Pijnappels DA, et al. (2007) Resynchronization of separated rat cardiomyocyte fields with genetically modified human ventricular scar fibroblasts. Circulation. 116: 2018-2028.

Pillekamp F, et al. (2012) Contractile properties of early human embryonic stem cell-derived cardiomyocytes: beta-adrenergic stimulation induces positive chronotropy and lusitropy but not inotropy. Stem Cells Dev. 21: 2111-2121.

Podratz J, et al. (2004) Antioxidants are necessary for myelination of dorsal root ganglion neurons, in vitro. Glia. 45: 54-58.

(56) References Cited

OTHER PUBLICATIONS

Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90: 1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and McMorris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B—Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly(ethylene glycol) Photolithography to Create High-Density Cell Arrays on Glass. Langmuir. 19: 9855-9862.
Reyes D, et al. (2004) Micropatterning neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine)/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation in apolipoprotein E deficient and human apolipoprotein E transgenic mice. Neuroscience. 98: 353-359.
Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci U S A. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-1. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. J Neurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-641.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-119.
Scherer J, et al. (1995) Differentiation and maturation of rabbit retinal oligodendrocyte precursor cells in vitro. Brain Res Dev Brain Res. 89: 214-226.

(56) References Cited

OTHER PUBLICATIONS

Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276: C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster R and Holzhutter HG. (1995) Use of mathematical models for predicting the metabolic effect of large-scale enzyme activity alterations. Application to enzyme deficiencies of red blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote M and Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KATP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.

Sheng Z, et al. (1996) Cardiotrophin-1 displays early expression in the murine heart tube and promotes cardiac myocyte survival. Development. 122: 419-428.
Sheridan DC, et al. (2003) Ca2+-dependent excitation-contraction coupling triggered by the heterologous cardiac/brain DHPR beta2a-subunit in skeletal myotubes. Biophys J. 85: 3739-3757.
Sheridan DC, et al. (2003) Truncation of the carboxyl terminus of the dihydropyridine receptor beta1a subunit promotes Ca2+ dependent excitation-contraction coupling in skeletal myotubes. Biophys J. 84: 220-237.
Sherman DL and Brophy PJ. (2005) Mechanisms of axon ensheathment and myelin growth. Nat Rev Neurosci. 6: 683-690.
Sherman DL, et al. (2005) Neurofascins are required to establish axonal domains for saltatory conduction. Neuron. 48: 737-742.
Shimono K, et al. (2000) Multielectrode Recording of Rhythmic Oscillations in Brain Slices: A Novel Technique for Screening Psychoactive Drugs. Faseb J. 14: 1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19: 317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313: 107-117.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. Acs Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-1729.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.

(56) References Cited

OTHER PUBLICATIONS

Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.
St. George-Hyslop PH and Petit A. (2005) Molecular biology and genetics of Alzheimer's disease. C R Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 79.
Stenger DA, et al. (1992) Coplanar Molecular Assemblies of Aminoalkylsilane and Perfluorinated Alkylsilane—Characterization and Geometric Definition of Mammalian-Cell Adhesion and Growth. Journal of the American Chemical Society. 114: 8435-8442.
Stenger DA, et al. (1993) Surface determinants of neuronal survival and growth on self-assembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology—mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison S and Mayne R. (1992) Formation of highly organized skeletal muscle fibers in vitro. Comparison with muscle development in vivo. J Cell Sci. 102: 643-652.

Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Sac Lond B Biol Sci. 202: 417-421.
Takashima Y, et al. (2007) Neuroepithelial cells supply an initial transient wave of MSC differentiation. Cell. 129: 1377-1388.
Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko YI, et al. (2007) Human fetal neural stem cells grafted into contusion-injured rat spinal cords improve behavior. J Neurosci Res. 85: 47-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-903.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT(4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu K and Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J. 19: 1592-1601.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.

(56) References Cited

OTHER PUBLICATIONS

Umbach JA, et al. (2012) Functional neuromuscular junctions formed by embryonic stem cell-derived motor neurons. PLoS One. 7: e36049.
Urakami H and Chiu AY. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through NO-synthase. Physiol Res. 44: 205-208.
Vakakis N, et al. (1995) In vitro myoblast to myotube transformations in the presence of leukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacal Toxicol Methods. 49: 171-181.
van de Ven C, et al. (2007) The potential of umbilical cord blood multipotent stem cells for nonhematopoietic tissue and cell regeneration. Exp Hematol. 35: 1753-1765.
van der Valk J, et al. (2010) Optimization of chemically defined cell culture media—replacing fetal bovine serum in mammalian in vitro methods. Toxicol In Vitro. 24: 1053-1063.
van Rijen HV, et al. (2006) Connexins and cardiac arrhythmias. Adv Cardiol. 42: 150-160.
van Soest PF and Kits KS. (1998) Conopressin affects excitability, firing, and action potential shape through stimulation of transient and persistent inward currents in molluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue culture: Effects on skeletal muscle organogenesis. In Vitro Cell Dev Biol. 24: 609-619.
Varghese K, et al. (2009) Regeneration and characterization of adult mouse hippocampal neurons in a defined in vitro system. J Neurosci Methods. 177: 51-59.
Varghese K, et al. (2010) A new target for amyloid beta toxicity validated by standard and high-throughput electrophysiology. PLoS One. 5: e8643.
Vargo TG, et al. (1992) Monolayer Chemical Lithography and Characterization of Fluoropolymer Films. Langmuir. 8: 130-134.
Vartanian T, et al. (1988) Oligodendrocyte substratum adhesion modulates expression of adenylate cyclase-linked receptors. Proc Natl Acad Sci U S A. 85: 939-943.
Ventimiglia R, et a. (1987) Localization of beta-adrenergic receptors on differentiated cells of the central nervous system in culture. Proc Natl Acad Sci U S A. 84: 5073-5077.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-L1 cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Z and Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.

Waggoner PS and Craighead HG. (2007) Micro- and nanomechanical sensors for environmental, chemical, and biological detection. Lab Chip. 7: 1238-1255.
Wagner I, et al. (2013) a dynamic multi-organ-chip for long-term cultivation and substance testing proven by 3D human liver and skin tissue co-culture. Lab Chip. 13: 3538-3547.
Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J Neurochem. 101: 1172-1184.
Walsh K, et al. (2005) Human central nervous system tissue culture: a historical review and examination of recent advances. Neurobiol Dis. 18: 2-18.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and ciliary neurotrophic factor on the proliferation and differentiation of adult human myoblasts. Cell Mol Neurobiol. 28: 113-124.
Ward JH, et al. (2001) Micropatterning of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122: R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann N Y Acad Sci. 605: 1-14.
Wright CD, et al. (2008) Nuclear alpha1-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.

(56) References Cited

OTHER PUBLICATIONS

Wu P, et al. (2002) Region-specific generation of cholinergic neurons from fetal human neural stem cells grafted in adult rat. Nat Neurosci. 5: 1271-1278.

Wu ZR, et al. (2007) Layer-by-layer assembly of polyelectrolyte films improving cytocompatibility to neural cells. J Biomed Mater Res A. 81: 355-362.

Wyart C, et al. (2002) Constrained synaptic connectivity in functional mammalian neuronal networks grown on patterned surfaces. J Neurosci Methods. 117: 123-131.

Xi J, et al. (2005) Self-assembled microdevices driven by muscle. Nat Mater. 4: 180-184.

Xu C, et al. (2006) Growth and differentiation of human embryonic stem cells for cardiac cell replacement therapy. Curr Stem Cell Res Ther. 1: 173-187.

Xu H, et al. (2008) Development of a stable dual cell-line GFP expression system to study estrogenic endocrine disruptors. Biotechnol Bioeng. 101: 1276-1287.

Xu L, et al. (2006) Human neural stem cell grafts ameliorate motor neuron disease in SOD-1 transgenic rats. Transplantation. 82: 865-875.

Xu T, et al. (2004) Construction of high-density bacterial colony arrays and patterns by the ink-jet method. Biotechnol Bioeng. 85: 29-33.

Xu T, et al. (2005) Inkjet printing of viable mammalian cells. Biomaterials. 26: 93-99.

Xu T, et al. (2006) Viability and electrophysiology of neural cell structures generated by the inkjet printing method. Biomaterials. 27: 3580-3588.

Xu T, et al. (2009) Electrophysiological characterization of embryonic hippocampal neurons cultured in a 3D collagen hydrogel. Biomaterials. 30: 4377-4383.

Yablonka-Reuveni Z. (1995) Development and postnatal regulation of adult myoblasts. Microsc Res Tech. 30: 366-380.

Yan J, et al. (2007) Extensive neuronal differentiation of human neural stem cell grafts in adult rat spinal cord. PLoS Med. 4: 318-332.

Yan Z, et al. (2002) Roscovitine: a novel regulator of P/Q-type calcium channels and transmitter release in central neurons. J Physiol. 540: 761-770.

Yang FS, et al. (2005) Curcumin inhibits formation of amyloid beta oligomers and fibrils, binds plaques, and reduces amyloid in vivo. J Biol Chem. 280: 5892-5901.

Yang J, et al. (2006) Synthesis and evaluation of poly(diol citrate) biodegradable elastomers. Biomaterials. 27: 1889-1898.

Yang L, et al. (2007) Increased asynchronous release and aberrant calcium channel activation in amyloid precursor protein deficient neuromuscular synapses. Neuroscience. 149: 768-778.

Yang LX and Nelson PG. (2004) Glia cell line-derived neurotrophic factor regulates the distribution of acetylcholine receptors in mouse primary skeletal muscle cells. Neuroscience. 128: 497-509.

Yang SY, et al. (2003) New class of ultrathin, highly cell-adhesion-resistant polyelectrolyte multilayers with micropatterning capabilities. Biomacromolecules. 4: 987-994.

Yang Y, et al. (2003) Neuronal cell death is preceded by cell cycle events at all stages of Alzheimer's disease. J Neurosci. 23: 2557-2563.

Yang Z, et al. (1999) Protein Interactions with Poly(ethylene glycol) Self-Assembled Monolayers on Glass Substrates: Diffusion and Adsorption. Langmuir. 15: 8405-8411.

Yankner BA. (1996) Mechanisms of neuronal degeneration in Alzheimer's disease. Neuron. 16: 921-932.

Yap FL and Zhang Y. (2007) Protein and cell micropatterning and its integration with micro/nanoparticles assembly. Biosens Bioelectron. 22: 775-788.

Yasuda SI, et al. (2001) A novel method to study contraction characteristics of a single cardiac myocyte using carbon fibers. Am J Physiol Heart Circ Physiol. 281: H1442-H1446.

Yeung CK, et al. (2007) Drug profiling using planar microelectrode arrays. Anal Bioanal Chem. 387: 2673-2680.

Yin SH, et al. (2005) Measuring single cardiac myocyte contractile force via moving a magnetic bead. Biophys J. 88: 1489-1495.

Zhao BL, et al. (1989) Scavenging effect of extracts of green tea and natural antioxidants on active oxygen radicals. Cell Biophys. 14: 175-185.

Zhou L, et al. (2005) Mechanistic model of cardiac energy metabolism predicts localization of glycolysis to cytosolic subdomain during ischemia. Am J Physiol Heart Circ Physiol. 288: H2400-H2411.

Zhou Z, et al. (1999) Block of HERG potassium channels by the antihistamine astemizole and its metabolites desmethylastemizole and norastemizole. J Cardiovasc Electrophysiol. 10: 836-843.

Zimmermann WH, et al. (2000) Three-dimensional engineered heart tissue from neonatal rat cardiac myocytes. Biotechnol Bioeng. 68: 106-114.

Zimmermann WH, et al. (2002) Tissue Engineering of a Differentiated Cardiac Muscle Construct. Circ Res. 90: 223-230.

Zorzano A, et al. (2003) Intracellular signals involved in the effects of insulin-like growth factors and neuregulins on myofibre formation. Cell Signal. 15: 141-149.

Zurn AD, et al. (1996) Combined effects of GDNF, BDNF, and CNTF on motoneuron differentiation in vitro. J Neurosci Res. 44: 133-141.

Zweigerdt R, et al. (2003) Generation of confluent cardiomyocyte monolayers derived from embryonic stem cells in suspension: a cell source for new therapies and screening strategies. Cytotherapy. 5: 399-413.

ated applicati> # SYNTHETIC MAMMALIAN NEUROMUSCULAR JUNCTION AND METHOD OF SCREENING FOR A CANDIDATE DRUG THEREON

RELATED APPLICATION

This application is a continuation of U.S. application Ser. No. 13/696,396 filed on Jan. 21, 2013, now U.S. Pat. No. 8,835,168, which is a national phase application of PCT/US2011/035585 filed on May 6, 2011, which claims priority to U.S. Provisional Application No. 61/332,003 filed on May 6, 2010 and which is a continuation-in-part application of U.S. application Ser. No. 12/765,996 filed on Apr. 23, 2010, now U.S. Pat. No. 8,815,584, which claims priority to U.S. Provisional Application No. 61/171,958 filed on Apr. 23, 2009, each application of which is herein incorporated by reference in its entirety.

STATEMENT OF GOVERNMENT INTEREST

This invention was made with government support under grant number R01NS050452 awarded by the National Institutes of Health. The government has certain rights in the invention.

FIELD OF THE INVENTION

The invention relates to the field of cell culture, and, more particularly, to formation of neuromuscular junctions.

BACKGROUND OF THE INVENTION

Neuromuscular junction ("NMJ") formation is a complex process that depends on many variables. Unfortunately, current techniques for producing NMJs suffer from one or more drawbacks which hinder their reproducibility and utility.

For centuries, animals and animal-derived tissues have been the major tools for understanding biological systems, human diseases, developing therapeutic strategies and screening drugs. However, translating animal data to clinical applications has been problematic, leading to fewer drugs being approved and an increasing cost in the drug discovery process (58). While some functional in vitro systems composed of human cells has been reported for liver (59), skin (60, 61) and cardiomyocytes (62, 63), no system composed of human cells has been reported for neuronal systems. Systems based on functional NMJs are of particular interest due to the fact that NMJs represents a synapse-based model that would be clinically applicable to spinal cord injury and motoneuron-related diseases such as Amyotrophic lateral sclerosis ("ALS") (64), spinal muscle atrophy (65) and muscular dystrophy (66). An in vitro (1) co-culture system composed of human motoneurons and skeletal muscle would be useful for studies ranging from understanding NMJ synaptogenesis, target generation for NMJ related diseases, screening therapeutic candidates and conducting drug toxicology evaluation. The advantages of human-based in vitro systems compared to in vivo systems reside in that they are much simpler and therefore easy to manipulate any factors, to dissect the mechanisms or pathways and to analyze the results.

One technique for forming NMJs in vitro to use a motoneuron ("MN")-muscle cell co-culture. MN-muscle co-cultures have been described in Xenopus (1, 2), chick (3-5), mouse (6, 7) and rat (8, 9), as well as in cross-species investigations between mouse MN-chick muscle (7, 10), human stem cell-derived MNs-myotubes from C2C12 cells (11).

One drawback to these in vitro MN-muscle co-culture systems is that they use serum containing media and a biological substrate (3-5, 8, 9). Since the serum containing medium contains many unknown components and because of the technical difficulties in creating reproducible biological substrates, these examples have led to undesired culture variability, making it extremely difficult, if not impossible, to ascertain the minimum factors required for recreating or maintaining the NMJ in vitro.

Due to the variability inherent with serum containing media (12), serum-free NMJ formation systems have been developed. NMJ formation in serum-free systems has been demonstrated using rat cells (13). Also, cross species NMJ formation between human MN and rat muscle (14) has been demonstrated. These in vitro systems comprised of animal-derived components have provided the scientific community with readily available models for understanding NMJ synaptogenesis and NMJ-related diseases, however, in order to understand NMJ formation in all human cells, the results from these systems must be extrapolated, which can be disadvantageous for clinical applications among others.

A major hurdle in building in vitro biological systems using human components is limitations related to tissue source. However, recent developments in stem cell biology provide an avenue to, not only have an unlimited supply of human cells for tissues, but also to provide genetic diversity in the systems. Cloned human skeletal muscle satellite cells have been used for studying NMJs in vitro by combining them with rat spinal explants or dissociated MN in serum-containing systems (15-19). MNs derived from human embryonic stem cells ("hESC") (11) and human fetal spinal cord stem cells ("hSCSC") (20) have been studied. NMJ formation has been (2) demonstrated between hESCs and C2C12 cells in a serum based system (11), as well as between hSCSCs and rat myotubes derived from embryonic skeletal muscles in a defined serum-free system (14). However, no human based in vitro NMJ system, in which both MNs and myotubes were derived from stem cells presently exists. Accordingly, there is a need in the art for a human based system for NMJ formation that does not suffer from one or more of the above described drawbacks.

SUMMARY

Certain embodiments of the invention are directed to methods that satisfy the need for a human based NMJ formation system. In one exemplary embodiment, the method comprises forming functional neuromuscular junctions between motoneurons and muscle cells by co-culturing one or more human motoneurons and one or more human muscle cells in a substantially serum-free medium.

In another embodiment the method comprises suspending human skeletal muscle cells in a serum-free medium; suspending human motoneurons derived from human spinal cord stem cells in the serum-free medium; plating the suspended muscle cells and the suspended motoneurons onto an artificial carrier; and monitoring for formation of functional neuromuscular junctions.

Other embodiments of the invention are directed to neuromuscular junctions that satisfy this need. In one example, the embodiment is directed to synthetic mammalian neuromuscular junction comprising a human motoneuron functionally linked to a human muscle cell in a substantially serum-free medium. The human motoneuron can be functionally linked to the human muscle cell on an artificial surface. A preferred artificial surface has a silicon based monolayer substrate deposited thereon, which may, if desired, be deposited in a predetermined pattern.

In certain embodiments, the substantially serum-free medium is completely serum free. Some examples of the substantially serum-free medium comprise at least one synaptogenesis promoting component and one or more trophic factors. NbActiv4 can be added to the serum-free medium. In a preferred embodiment, the medium comprises the components in Table 1.

Preferably, but not necessarily, the human motoneuron cells are derived from human spinal cord stem cells and the human muscle cells are derived from human skeletal muscle stem cells.

Some embodiments can include a synthetic substrate adapted to support at least one neuromuscular junction thereon. The synthetic substrate is preferably silicon based and more preferably is DETA. The synthetic substrate may be deposited on a support surface in a predetermined pattern if desired. The synthetic substrate may be coated on a carrier.

These and other objects, aspects, and advantages of the present invention will be better appreciated in view of the drawings and following detailed description of the preferred embodiments.

DETAILED DESCRIPTION OF THE PREFERRED EMBODIMENT

Figure 1:
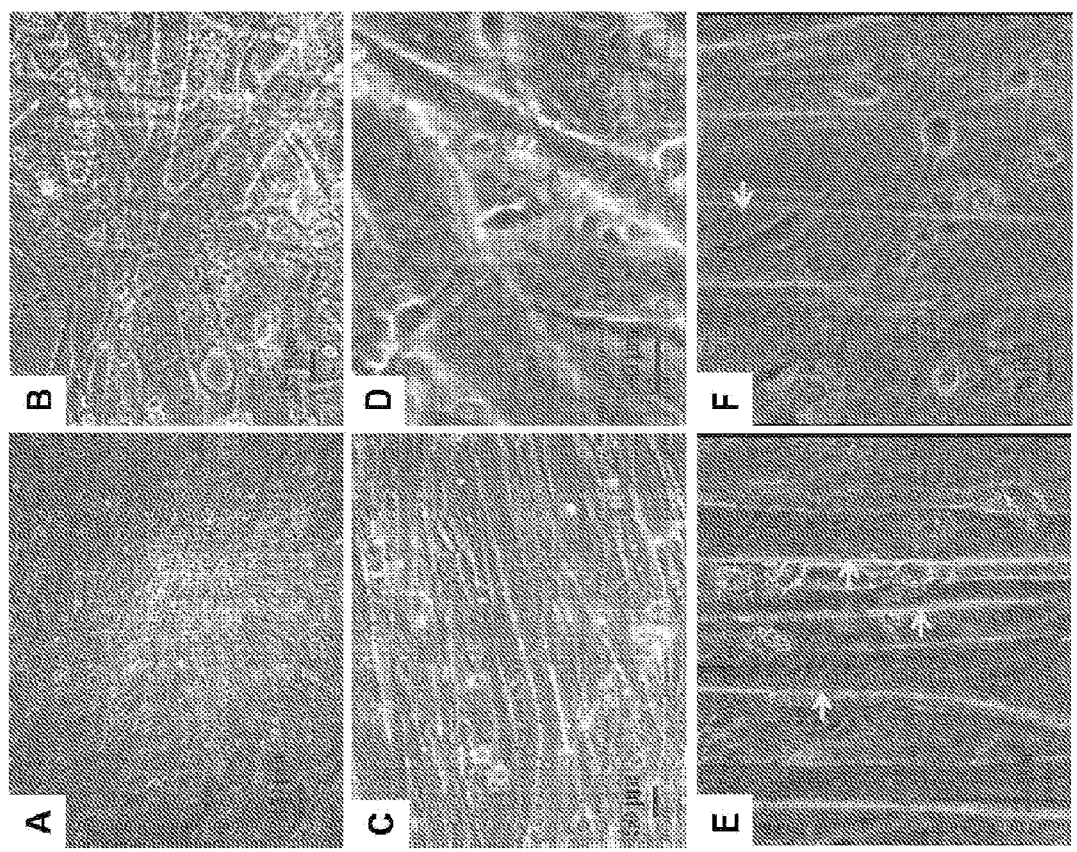
FIG. 1 is a set of phase contrast microscopy images showing human skeletal muscle cells (hSKMs) and human motoneurons (hMNs) in culture and co-culture, according to an embodiment of the present invention; A. Depicts myocytes that were allowed to grow to confluency before differentiation was induced; B. Depicts, multi-nuclei myotubes that were induced during differentiation; C. Depicts both myotubes and neurons that survived in the co-culture; D. Illustrates connections between neurons and myotubes in the co-culture (indicated by arrows); E. Shows the striation of myotube as indicated by the arrow; F. Illustrates a neuron with MN morphology sends out long axons towards a striated myotube as indicated by the arrow.

In the Summary of the Invention above and in the Detailed Description of the Invention and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully with reference to the accompanying drawings, in which preferred embodiments of the invention are shown. This invention may, however, be embodied in many different forms and should not be construed as limited to the embodiments set forth herein.

According to an embodiment of the invention, an in vitro system for forming NMJs between human cells is provided. The system comprises an in vitro co-culture adapted to allow NMJs to form between human neurons and human muscle cells in a defined environment. The defined environment is preferably achieved by utilizing a co-culture medium in which the ingredients and quantities of those ingredients are known. In a preferred embodiment, the medium contains no serum. The co-culture can also be prepared on substrate that has a defined surface, such as by assembling a synthetic material onto an underlying surface for example. In some cases, the synthetic material can be assembled on the underlying surface according to a desired pattern.

In vitro NMJ co-culture systems containing human cellular components have been reported previously. Human stem cell-derived motoneurons can form NMJs when co-cultured with C2C12 cells (11) from co-cultures of embryonic rat spinal explants with human SKM stem cell-derived myofibers (17, 32), but in serum containing media. One study also investigated human stem cell derived motoneuron innervations for rat embryonic SKM in a defined system (14). These systems were employed to study the functional integrity of motoneurons differentiated from human stem cells (11, 14), to investigate the functional maturation process of SKMs derived from human SKM stem cells (33, 34), the mechanisms of NMJ formation on human SKMs (15-19, 30-36), and the pathogenesis of some spinal muscular diseases (37).

This disclosure reports the first human-based in vitro NMJ system which supports the differentiation of human stem cell derived motoneurons and SKMs and provides for functional NMJ formation. The system developed in this study, by the co-culture of human stem cell-derived motoneurons and SKMs, provides a system closer to the human condition that is capable of addressing the above described drawbacks, as well as neurological and/or muscular disease modeling, drug discovery and regenerative medicine.

In an exemplary embodiment, the human neurons are MNs differentiated from human spinal cord stem cells and the muscle cells are human skeletal muscle stem cells.

By way of example, a suitable co-culture medium that can be used in the human NMJ formation system is comprised of the ingredients provided in Table 1. The scope of the invention is not limited only to these ingredients, nor is it required that every one of the ingredients be used in every embodiment. Ingredients may be added to or taken away from Table 1 without falling outside the scope of the invention. The combination of NEUROBASAL™ medium, B27, Glutamax, GDNF, BDNF, Shh, RA, IGF-1, cAMP, CNTF, NT-3, NT-4, Vitronectin and Laminin has been found to be able to support the growth, differentiation, and long-term survival of MNs derived from human stem cells (11, 14). Laminins are important components of the extracellular matrix that facilitates synaptogenesis (1). Specifically, β2 laminins are concentrated at synaptic sites and are useful for their postnatal maturation (57). The addition of the G5 supplement to the co-culture medium has been found to significantly enhance myocyte proliferation. However, the continuous presence of these trophic factors, including BDNF, GDNF, NT-3, NT-4 and cAMP, was found to significantly down regulate agrin deposition along the neurites and at nerve-muscle contacts, thus preventing synaptogenesis (2).

In a preferred preparation of NMJs, the trophic factors were gradually withdrawn and the culture was fed using only NbActiv4 media. The NbActiv4 media formula was generated by adding three ingredients, cholesterol, estrogen, and creatine to media containing NEUROBASAL™, B27 and Glutamax (53). There is evidence that the addition of these ingredients can significantly promote synaptogenesis (53-56). Therefore, the co-culture was first plated in the co-culture medium to ensure the survival and growth of MNs and myocytes, followed by the gradual withdrawal of these factors which enabled the reciprocal induction between the MNs and myotubes that naturally occurs in development.

Advantageously, the defined co-culture medium delineates the basis for the essential components during NMJ formation, and provides a basic system for dissecting the individual factors, for investigating the underlying mechanisms, and later for treatment of diseases related to the cellular components of NMJs.

A preferred substrate is trimethoxysilylpropyldiethyl-enetri-amine ("DETA"), which can be coated onto a carrier or surface such as a glass cover slip for example. In the working examples discussed below, DETA was coated on a glass surface to form a self-assembled monolayer. DETA has previously been shown to support neuronal (26), skeletal muscle (27), endothelial (38), and cardiac cell growth (39), and has been used in creating high-resolution, in vitro patterned circuits of embryonic hippocampus neurons (40). Moreover, DETA substrates have been shown to promote guided axonal growth and direct axonal and dendritic process extension at the level of a single neuron (41). Therefore, the successful formation of NMJ on this substrate implies that some co-cultures of the invention can be patterned at high resolution to study engineered in vitro NMJs. Especially, this surface modification technique can be used for guiding specific NMJ formation.

Functional in vitro systems composed of human cells in a defined, serum-free system, especially those reproducing fundamental neurological processes, will be a significant component in transforming current methods of drug discovery and toxicology. The utilization of neuronal systems derived from stem cells enables a process that can be genetically diverse, yet source reproducible. The use of a defined, serum-free system also enables the integration into the next generation of high-content and ultimately high-throughput screening technologies.

Accordingly, embodiments of the invention have many advantages. Some, but not all, of those advantages are listed here. Not all of these advantages are required by all embodiments of the invention. In summary, embodiments of the invention provide the first pure human based NMJ in vitro culture system. This human cell-based system bridges the gap between findings from animals and their clinical applications. The stem cell origin for both motoneurons and skeletal muscles enables the formation of these cultures in large quantities which can be important for high throughput drug screening. The serum-free medium allows this system to be highly re-producible and easy to manipulate. The patternable surface gives the power to the system to be engineered into neural circuits. These attributes indicate that this system will facilitate not only the studies concerning human NMJ development and regulation, both in vitro and in vivo, but also the research fields targeting NMJ-related diseases and treatment, such as by developing high information content drug screen systems and test beds in pre-clinical studies.

In the following section, we describe several working examples in which an exemplary human NMJ model system embodiment was characterized by morphology, immunocytochemistry, and electrophysiology. Further, NMJ formation was demonstrated by immunocytochemistry and videography.

WORKING EXAMPLES

DETA Surface Modification

Glass coverslips (6661F52, 22×22 mm No. 1; Thomas Scientific, Swedesboro, N.J., USA) were cleaned using HCl/methanol (1:1) for at least 2 hours, rinsed with water, soaked in concentrated H2S04 for at least 2 hours and rinsed with water. Coverslips were boiled in nanopure water and then oven dried. The trimethoxysilylpropyldiethylenetri-amine (DETA, T2910KG; United Chemical Technologies Inc., Bristol, Pa., USA) film was formed by the reaction of cleaned surfaces with a 0.1% (v/v) mixture of the organosilane in freshly distilled toluene (T2904; Fisher, Suwanne, Ga., USA). The DETA coated coverslips were heated to ~80° C., then cooled to room temperature (RT), rinsed with toluene, reheated to approximately the same temperature, and then cured for at least 2 hours at 110 C. Surfaces were characterized by contact angle and X-ray photoelectron 5 spectroscopy as described previously (26, 42, 43).

Co-culture of Human MNs and Human Skeletal Muscle Stem Cells

Materials and Methods. The human spinal cord stem cell line was isolated and established as described in (44-46). MNs were differentiated from this cell line as described in (20). Briefly, ~1×10$^6$ hSCSCs were plated in one 60 mm paranox cell culture dish (Nunc, Cat #174888) and differentiated 4 days in the priming media followed by 6 days in differentiation media. The composition of the priming media and differentiation media were described in (20).

Human skeletal muscle stem cells (hSKM SCs) were isolated, proliferated and differentiated as described in (47). Briefly, primary human skeletal muscle cells isolated by needle biopsy (48) were expanded in myoblast growth medium (MGM; SkGM (Cambrex Bio Science, Walkersville, Md.) plus 15% (v/v) fetal bovine serum). Biopsies were performed on adult volunteers according to procedures approved by the Institutional Clinical Review Board of the Miriam Hospital. Cell preparations on average were 70% myogenic based on desminpositive staining (49). Myoblast fusion into post-mitotic myofibers was induced by incubation in differentiation medium (high-glucose DMEM (Invitrogen, Carlsbad, Calif.) supplemented with insulin (10 μg/ml), bovine serum albumin (50 μg/ml), epidermal growth factor (10 ng/ml) and gentamicin (50 μg/ml)). For each culture, hSKM SCs were plated on DETA coverslips at a density of 20 cells/mm$^2$ in hSKM Growth Medium (Lonza, Cat# CC-3160), fed every 2 days by changing the whole medium. On day 7, myoblast fusion was induced by switching to differentiation medium. The cells were fed every 2 days by changing half of the medium. On day 7 after differentiation, differentiated hSCs were harvested and plated on top of these induced myotubes in a density of 200 cells/mm$^2$, and the medium was changed to co-culture medium (Table 1). Two days later, the medium was fed by co-culture medium (without G5) by changing half of the medium. After another two days and thereafter, the cultures were fed by NBactiv4 (Brain Bits) by changing half of the medium.

Discussion. The procedure of co-culturing motoneurons and skeletal muscles (SKMs) was described in detail in the Material and Methods. Briefly, human SKM stem cells were allowed to grow to confluence before induction of differentiation (FIG. 1A). After switching to differentiation media, the fusion of myocytes was initiated. Multi-nuclei myotubes formed gradually and were prevalent from day 4 in the culture (FIG. 1B). Differentiated human motoneurons (hMNs) were cultured as in Guo et al. (20) and were plated on the top of the differentiated myotubes and the medium was switched to a co-culture medium at this time. Both hSKMs and hMNs survived well in the co-culture media (FIG. 1C). Also, the differentiation of both hMNs and hSKMs were evident after one week. The hMNs were easily identifiable in the co-culture and sent out axons either along or ending at the myotubes (FIGS. 1D, E). In addition, a large number of human myotubes exhibited striated band patterns (FIGS. 1E, F). This characteristic A & I band patterning is caused by differential light diffraction due to the organization of myofibrial proteins forming sarcomeres within the myotubes, and is observed with mature in vivo muscle fibers (21, 22). The striated patterns indicated the formation of the basic contractile apparatus for skeletal muscle, implying that these myofibers were structurally and functionally mature.

Multiple plating conditions were examined to determine the optimal culturing procedures. When plating differentiated motoneurons on top of SKMs before extensive myotube formation the myocyte fusion proceeded sub-optimally when switched to the co-culture medium, and with the formation of a minimal number of multi-nuclei myotubes. The viability and morphological differentiation of the replated motoneurons was also poor, overall indicating that the co-culture media is not favorable for the fusion of human myocytes, and the successful replating of motoneurons required the pre-differentiation of the SKMs. This is reasonable considering that muscle cells release the neurotrophins BDNF, GDNF and NT-3/4 to support MN survival and attract neurite outgrowth of motoneurons during development (23-25).

Another observation was that when the co-culture was fed for four days with co-culture medium containing G5, undesired proliferation from undifferentiated stem cells was observed. When G5 was removed from the co-culture medium completely, however, the replated motoneurons survived poorly. To mediate this complication, the G5 was kept in the original plating medium for the co-culture and then was gradually removed after two days.

Immunocytochemistry and Microscopy

Materials and Methods. Cells on DETA coverslips were fixed in freshly prepared 4% paraformaldehyde for 15 min. For the co-stainings with BTX-488, cultures were incubated with BTX-488 (Invitrogen, Cat# B13422) at $1\times10^{-8}$M for 1 hr in the 37° C. incubator before fixation. Cells were then washed twice in Phosphate Buffered Saline (PBS) (pH 7.2, w/o $Mg^{2+}$, $Ca^{2+}$) for 10 min each at room temperature, and permeabilized with 0.1% triton X-100/PBS for 15 min. Non-specific binding sites were blocked in Blocking Buffer (5% Donkey serum plus 0.5% BSA in PBS) for 45 min at room temperature. Cells were then incubated with primary antibodies overnight at 4° C. After being washed with PBS 3×10 min, the cells were incubated with secondary antibodies for 2.5 hours at room temperature. The cells were then washed with PBS 3×10 min and mounted with Vectorshield with 4'-6-Diamidino-2-Phenylindole (dapi) (Vector laboratories, Inc.). Primary antibodies used in this study include: Rabbit-anti-β III Tubulin (Sigma, 1:1500), Mouse-anti-synaptophysin (Antibodies Inc., 1:100). The monoclonal antibody against muscle heavy chain (MHC, F1.625, 1:10) was obtained from the Developmental Studies Hybridoma Bank which is under the auspices of the NICHD and maintained by the University of Iowa. Secondary antibodies include: Donkey-anti-Mouse-488 (Invitrogen, 1:250) and Donkey-anti-Rabbit-594 (Invitrogen, 1:250). All antibodies were diluted in Blocking Buffer.

Figure 2:
FIG. 2 is a set of microscopy images showing that after one week of co-culture the morphology of hMNs and hSKM myofibers were well defined and easily distinguishable; A & B. Shows a neuron sent an axon towards a myotube and branched at the contacts with myotubes as indicated by the arrows; C. Depicts co-immunostaining of MHC (myosin heavy chain) with β III Tubulin in a 19 day co-culture.
Figure 2:
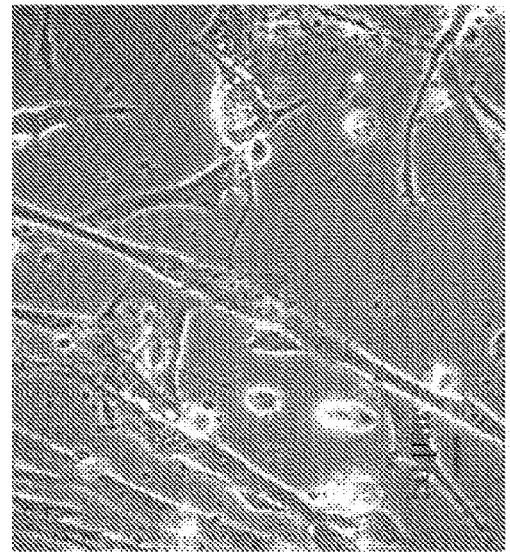
Figure 2:
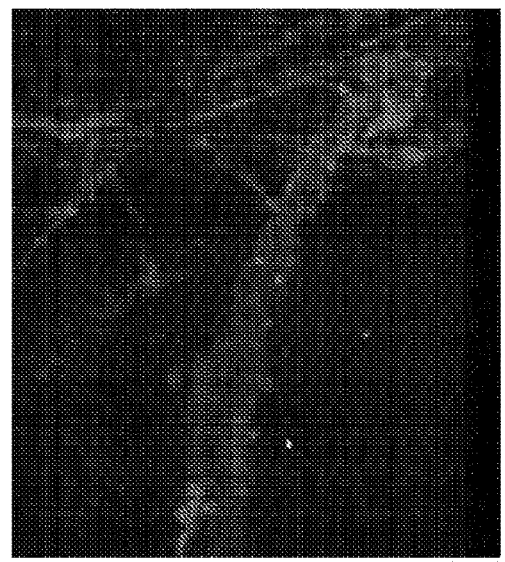
Figure 2:
Figure 2:
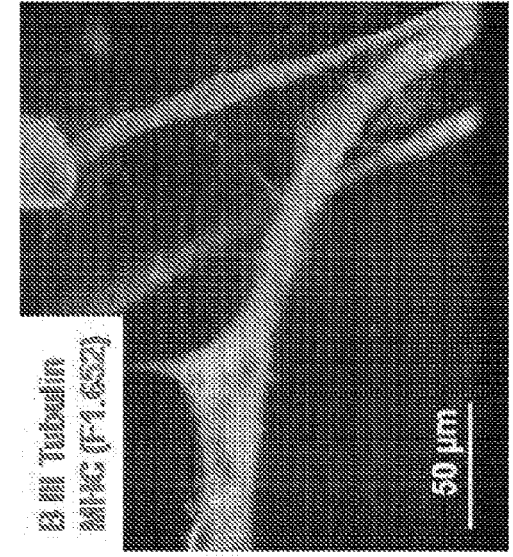
Figure 3:
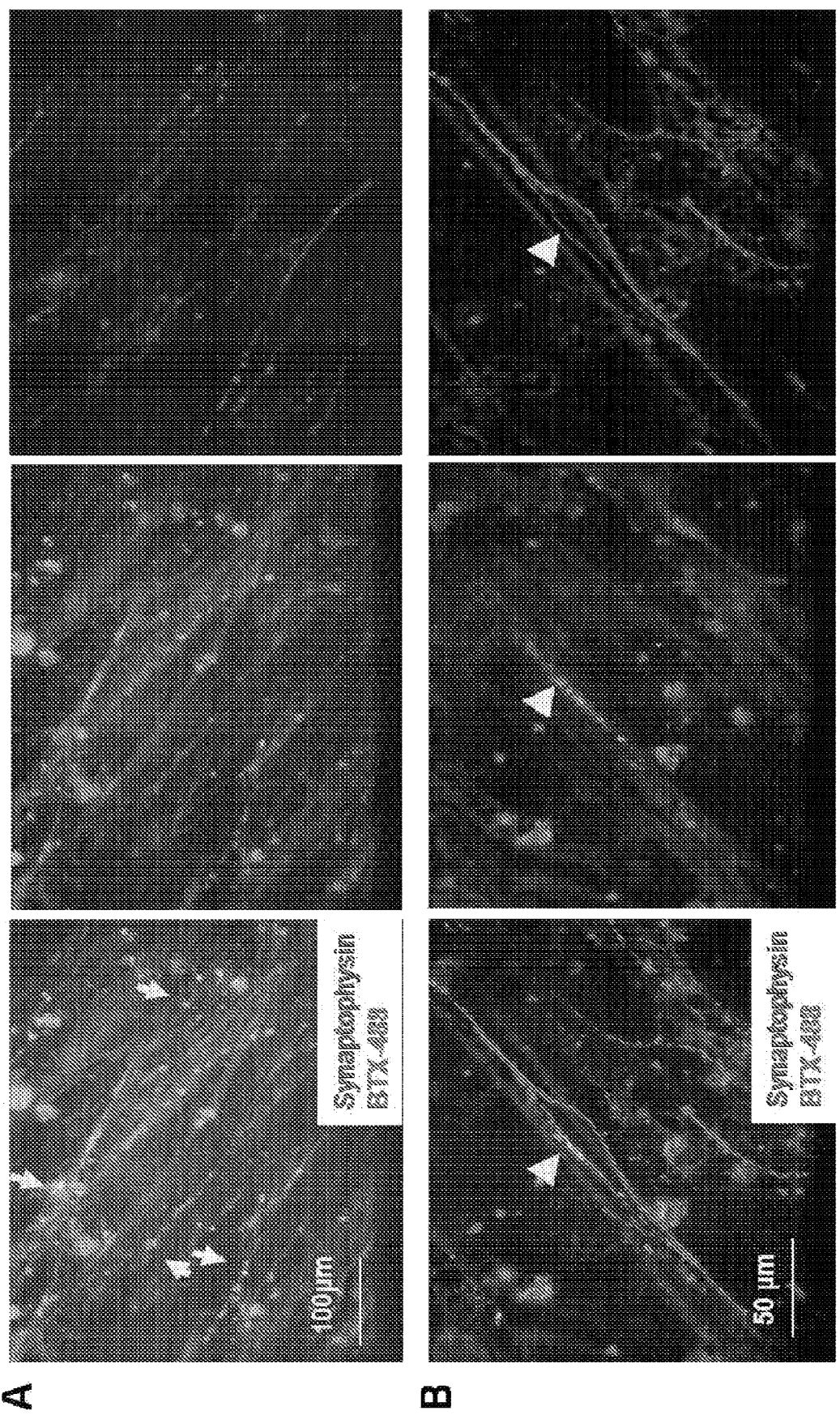
FIG. 3 is a set of microscopy images depicting synaptophysin-positive terminals co-localized with AchR clusters; potential synaptic sites (arrows) demonstrated by co-localization of nerve terminals (indicated by synaptophysin) and AchR (indicated by BTX488), in a day 15 coculture—Scale Bars A. 20×. B. 40×.

Discussion. After one week of co-culture, the morphology of hMNs and hSKM myofibers were well defined and easily distinguishable, and it was observed that the hMNs axons terminated and even branched at the contact with myofibers (FIGS. 2A, B). Utilizing immunocytochemical analysis with β-III Tubulin for neurons and muscle heavy chain (MHC) for the myofibers, the details of these contacts were confirmed. In the co-culture system the nerve endings branched in the vicinity of myotube and the terminals wrapped around the myotubes as shown in FIG. 2C. This image reproduces previous findings during NMJ formation which indicated that synaptogenesis is a dynamic process directly correlated to the active branching and remodeling of axon terminal arbors (28, 29). The potential for NMJs in the culture were further analyzed by the co-immunostaining of BTX-488 (a-bungarotoxin, Alexa Fluor® 488 conjugate) and synaptophysin, a synaptic vesicle protein. As shown in FIG. 3, synaptophysin positive terminals co-localized with AchR clusters, a strong indication for NMJ formation.

Electrophysiological Properties

Materials and Methods. Electrophysiological properties of spinal cord stem cell-derived motoneurons and human myotubes were investigated after ~10 days in the coculture using whole-cell patch-clamp recording techniques (26). The recordings were performed in a recording chamber located on the stage of a Zeiss Axioscope 2FS Plus upright microscope (50).

Motoneurons were identified visually under an infrared DIC videomicroscope. The largest multipolar or round cells (15-25 μm diameter) with bright illuminance in the culture were tentatively identified as motoneurons (51, 52). Patch pipettes with a resistance of 6-10 MO were made from borosilicate glass (BF 150-86-10; Sutter, Novato, Calif.) with a Sutter P97 pipette puller (Sutter Instrument Company).

Current-clamp and voltage-clamp recordings were made utilizing a Multiclamp 700A amplifier (Axon, Union City, Calif.). The pipette (intracellular) solution contained (in mM) K-gluconate 140, $MgCl_2$ 2, Na2ATP 2, Phosphocreatine 5, Phosphocreatine kinase 2.4 mg, Hepes 10; pH 7.2. After the formation of a gigaohm seal and the membrane puncture, the cell capacitance was compensated. The series resistance was typically <23 MO, and it was compensated >60% using the amplifier circuitry. Signals were filtered at 3 kHz and sampled at 20 k Hz using a DIGIDATA™1322A interface (Axon instrument).

Data recording and analysis were performed with pClamp8 software (Axon instrument). Membrane potentials were corrected by subtraction of a 15 mV tip potential, which was calculated using Axon's pClamp8 program. Membrane resistance and capacitance were calculated using 50 ms voltage steps from −85 to −95 mV without any whole-cell or series resistance compensation. The resting membrane potential and depolarization-evoked action potentials were recorded in current-clamp mode. Depolarization-evoked inward and outward currents were examined in voltage-clamp mode.

Monitoring the contraction of human skeletal muscles in the co-culture and the determination of the effect of (+)-tubocurarine chloride pentahydrate (tubocurarine or curare) on the NMJs by video recording.

Discussion.

Figure 4:
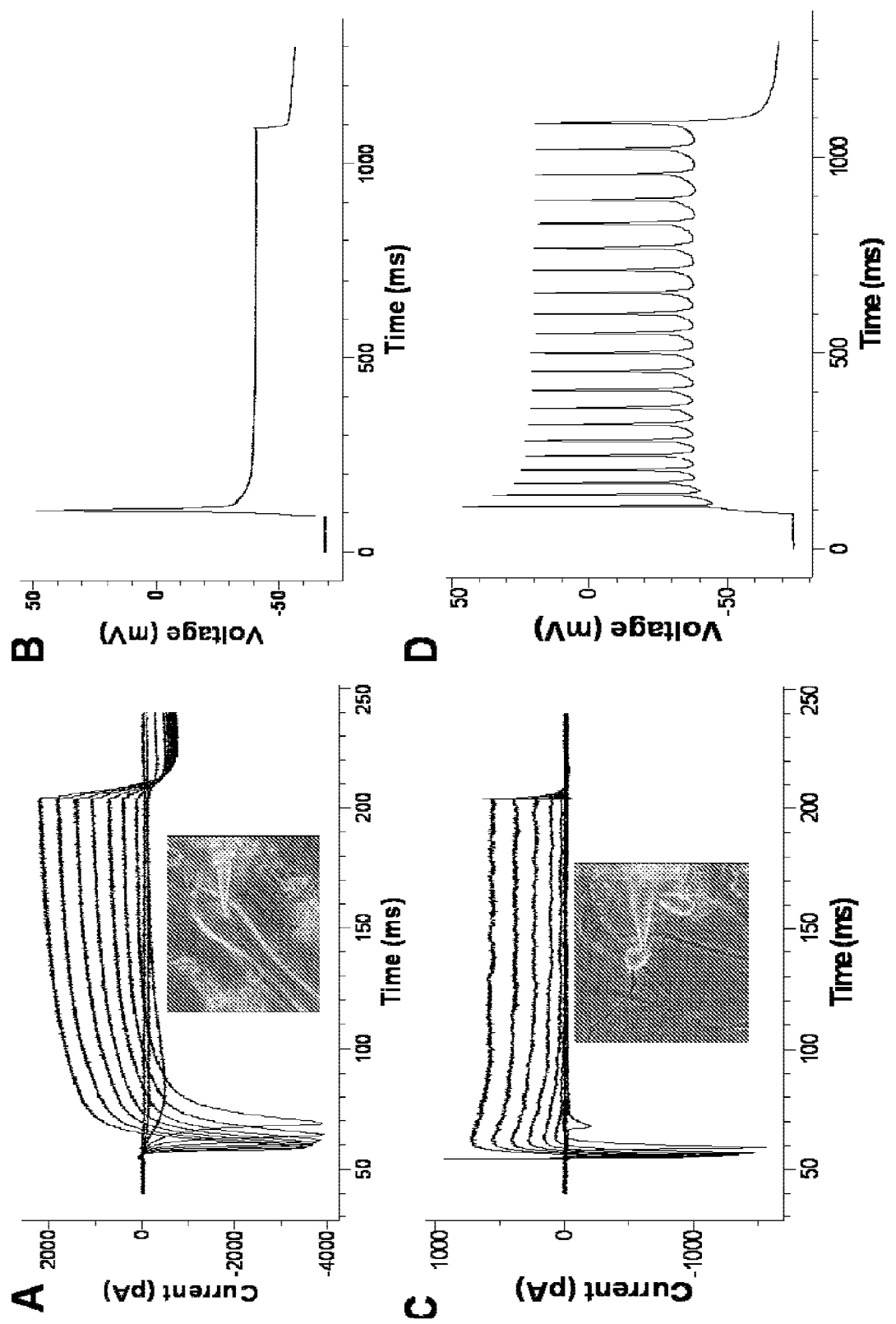
FIG. 4 is a representative graph of voltage-clamp and current-clamp recordings for the MNs and myotubes; A&B. Representative Voltage clamp (A) and Current clamp (B) trace recording on myotubes in the co-culture; C&D. Representative Voltage clamp (C) and Current clamp (D) trace Recording on motoneurons in the co-culture.

The electrophysiological properties of the MNs and myotubes in the co-culture were evaluated using voltage and current clamp recordings for each cellular component. Representative voltage-clamp and current-clamp recordings for the MNs and myotubes are shown in FIG. 4. The electrical properties of MNs in the co-culture system, such as membrane resistance, resting membrane potential, Na+/K+ current amplitude, the ability to repetitively fire and the amplitude of action potential (AP), were comparable to results described previously (20, 26). The electrical properties for the myotubes were also comparable to previously published results (27).

Videography of NMJ Formation

Materials and Methods. Functional NMJ formation was investigated in the co-culture system 1-2 weeks after MN plating utilizing video recordings. In each experiment, the coverslip in a 6-well plate was maintained in NBActiv media in a time lapse chamber (37° C., 5% $CO_2$) located on the stage of a Zeiss AXIOVERT™ microscope 200. The videos were recorded by a Hamamatsu digital camera (Model C848405G) at a frame rate of 8 frames/sec using Windows Movie Maker software. For the experiments with curare, 100 µl of the Nicotinic cholinergic antagonist, (+)tubocurarine chloride pentahydrate (also known as curare, cat. no. 93750, Sigma) (stock 250 µM, final 8 µM) was applied to the bath solution to block the acetylcholine receptors present in the NMJs. This concentration was chosen based on previous study (43).

Discussion.

The results obtained from several of the videos will now be discussed. In Video 1 (10 min), during the first 6 min, the myotube contracted in pulses which was recurrent approximately every 1-2 min. The contraction then stopped after this time period. In Video 2 (15 min), the contraction pulses of three spots were observed to intermittently contract. In Video 3 (15 min), myotube contraction was recorded for 7 min. The addition of Curare (5 µM) silenced the contraction. In Video 4 (22 min), myotube contraction was recorded for 11 min. The addition of Curare (5 µM) silenced the contraction.

Numerous muscle contractions in the absence of any stimulus could be observed in the co-culture approximately one week after the introduction of hMNs this was based on observations from more than 15 coverslips out of 5 independent platings. All videograph experiments were conducted in a system in which the cultures were kept in the chamber at 5% $CO_2$ 37 C conditions. They would stop in ambient condition soon after (within minutes) being taken out of the incubator. Contractions with a constant rhythm in the hMN-hSKM co-cultures were present as in Video 2, as well as contractions exhibiting a constant pattern of intermittent pulses as demonstrated in Video 1. Video 1 indicated a myotube contracting in pulses with an approximately 1-2 min interval. These recurrent contractions lasted for 6 min and stopped thereafter. In Video 2, recorded from another site, three other areas were shown to contract on and off intermittently. The contractions in the hMN-hSKM co-culture were tested by tubocurarine for their source of initiation. As in Video 3 and Video 4, the contractions ceased after the application of 100 ul of tubocurarine (200 uM) to the culture (final 5 µM), confirming the neuronal initiation of these contractions and the formation of NMJs. This experiment with curare was repeated 4 times with the same result.

These muscle contractions revealed a few differences compared to the co-cultures of hMN with rat embryonic SKMs (14). Although studies from co-cultures of fetal rat spinal cord explant with human myoblasts consistently indicated that hSKMs didn't have spontaneous contraction and any contraction in the co-culture was an indication of innervations (16-19, 30, 31).

The present invention has been described hereinabove with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical figures expressed herein are intended to be approximate and not an exact or critical figure unless expressly stated to the contrary.

Further, any publications, patent applications, patents, and other references mentioned herein are incorporated by reference in their entirety as if they were part of this specification. However, in case of conflict, the present specification, including any definitions, will control. In addition, as noted above, materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

Any element in a claim that does not explicitly state "means for" performing a specified function, or "step for" performing a specified function, is not to be interpreted as a "means" or "step" clause as specified in 35 U.S.C. §112, ¶ 6. In particular, the use of "step of" in the claims herein is not intended to invoke the provisions of 35 U.S.C. §112, ¶ 6.

References Cited

1. B. Lu, A. J. Czernik, S. Popov, T. Wang, M. M. Poo, P. Greengard: Expression of synapsin I correlates with maturation of the NMJ synapse. Neuroscience, 74:1087-1097 (1996).
2. H. B. Peng, J. F. Yang, Z. Dai, C. W. Lee, H. W. Hung, Z. H. Feng, C. P. Ko: Differential effects of neurotrophins and Schwann cell-derived signals on neuronal survival/growth and synaptogenesis. J Neurosci, 23:5050-5060 (2003).
3. G. D. Fischbach: Synapse formation between dissociated nerve and muscle cells in low density cell cultures. Developmental Biology, 28:407429 (1972).
4. G. D. Fischbach, S. A. Cohen: The distribution of acetylcholine sensitivity over uninnervated and innervated muscle fibers grown in cell culture. Developmental Biology, 31:147-162 (1973).
5. E. Frank, G. D. Fischbach: Early events in neuromuscular junction formation in vitro. J Cell Biol, 83:143-158 (1979).
6. J. M. Harper, C. Krishnan, J. S. Darman, D. M. Deshpande, S. Peck, I. Shats, S. Backovic, J. D. Rothstein, D. A. Kerr:

Axonal growth of embryonic stem cell-derived motoneurons in vitro and in motoneuron-injured adult rats. PNAS, 101:7123-7128 (2004).
7. G. B. Miles, D. C. Yohn, H. Wichterle, T. M. Jessell, V. F. Rafuse, R. M. Brownstone: Functional properties of motoneurons derived from mouse embryonic stem cells. Journal Of Neuroscience, 24:7848-7858 (2004).
8. M. P. Daniels, B. T. Lowe, S. Shah, J. X. Ma, S. J. Samuelson, B. Lugo, T. Parakh, C. S. Uhm: Rodent nerve-muscle cell culture system for studies of neuromuscular junction development: Refinements and applications. Microscopy Research and Technique, 49:26-37 (2000).
9. E. K. Dutton, C. S. Uhm, S. J. Samuelsson, A. E. Schaffner, S. C. Fitzgerald, M. P. Daniels: Acetylcholine receptor aggregation at nerve-muscle contacts in mammalian cultures: Induction be ventral spinal cord neurons is specific to axons. J Neurosci, 15:7401-7416 (1995).
10. P. Soundararajan, B. W. Lindsey, C. Leopold, V. F. Rafuse: Easy and rapid differentiation of embryonic stem cells into functional motoneurons using Sonic Hedgehog-producing cells. Stem Cells, 25:1697-1706 (2007).
11. X. J. Li, Z. W. Du, E. D. Zarnowska, M. Pankratz, L. O. Hansen, R. A. Pearce, S. C. Zhang: Specification of motoneurons from human embryonic stem cells. Nature Biotechnology, 23:215-221 (2005).
12. K. Walsh, J. Megyesi, R. Hammond: Human central nervous system tissue culture: a historical review and examination of recent advances. Neurobiology of Disease, 18:2-18 (2005).
13. M. Das, J. W. Rumsey, N. Bhargava, M. Stancescu, J. J. Hickman: A defined long-term in vitro tissue engineered model of neuromuscular junctions. Biomaterials, 31:4880-4888 (2010).
14. X. F. Guo, M. Das, J. W. Rumsey, M. Gonzalez, M. Stancescu, J. J. Hickman: NMJ formation between human stem cell derived motoneurons and rat skeletal muscle in a defined system. Tissue Engineering: Part C, 16(6): 1347-1355 (2010).
15. N. Gajsek, M. Jevsek, T. Mars, K. Mis, S. Pirkmajer, J. Brecelj, Z. Grubic: Synaptogenetic mechanisms controlling postsynaptic differentiation of the neuromuscular junction are nerve-dependent in human and nerve-independent in mouse C2C12 muscle cultures. Chemico-Biological Interactions, 175:50-57 (2008).
16. S. Guettier-Sigrist, G. Coupin, J.-M. Warter, P. Poindron: Cell Types Required to Efficiently Innervate Human Muscle Cells in vitro. Experimental Cell Research, 259: 204-212 (2000).
17. T. Kobayashi, V. Askanas, W. K. Engel: Human muscle cultured in monolayer and cocultured with fetal rat spinal cord: importance of dorsal root ganglia for achieving successful functional innervation. J Neurosci, 7:3131-3141 (1987).
18. T. Mars, M. P. King, A. F. Miranda, W. F. Walker, K. Mis, Z. Grubic: Functional innervation of cultured human skeletal muscle proceeds by two modes with regard to agrin effects. Neuroscience, 118:87-97 (2003).
19. T. Mars, K. J. Yu, X.-M. Tang, A. F. Miranda, Z. Grubic, F. Cambi, M. P. King: Differentiation of glial cells and motor neurons during the formation of neuromuscular junctions in cocultures of rat spinal cord explant and human muscle. Journal of Comparative Neurology, 438: 239-251 (2001).
20. X. F. Guo, K. Johe, P. Molnar, H. Davis, J. J. Hickman: Characterization of a human fetal spinal cord stem cell line NSI-566RSC and its induction to functional motoneurons. Tissue Engineering and Regenerative Medicine, 4:181-193 (2010).
21. B. E. Flucher, J. L. Phillips, J. A. Powell, S. B. Andrews, M. P. Daniels: Coordinated development of myofibrils, sarcoplasmic reticulum and transverse tubules in normal and dysgenic mouse skeletal muscle, in vivo and in vitro. Developmental Biology, 150:266-280 (1992).
22. A. Kontrogianni-Konstantopoulos, M. A. Ackermann, A. L. Bowman, S. V. Yap, R. J. Bloch: Muscle Giants: Molecular Scaffolds in Sarcomerogenesis. Physiol Rev, 89:1217-1267 (2009).
23. H. Funakoshi, N. Belluardo, E. Arenas, Y. Yamamoto, A. Casabona, H. Persson, C. F. Ibanez: Muscle-derived neurotrophin-4 as an activity-dependent trophic signal for adult motor neurons. Science, 268:14951499 (1995).
24. C. E. Henderson, H. S. Phillips, R. A. Pollock, A. M. Davies, C. Lemeulle, M. Armanini, L. Simmons, B. Moffet, R. A. Vandlen, L. C. Simpson, et al.: GDNF: a potent survival factor for motoneurons present in peripheral nerve and muscle. Science, 266:1062-1064 (1994).
25. A. D. Zurn, L. Winkel, A. Menoud, K. Djabali, P. Aebischer: Combined effects of GDNF, BDNF, and CNTF on motoneuron differentiation in vitro. Journal of Neuroscience Research, 44:133-141 (1996).
26. M. Das, P. Molnar, H. Devaraj, M. Poeta, J. Hickman: Electrophysiological and morphological characterization of rat embryonic motoneurons in a defined system. Biotechnology Progress, 19:1756-1761 (2003).
27. M. Das, C. A. Gregory, P. Molnar, L. M. Riedel, J. J. Hickman: A defined system to allow skeletal muscle differentiation and subsequent integration with silicon microstructures. Biomaterials, 27:4374-4380 (2006).
28. B. Alsina, T. Vu, S. Cohen-Gory: Visualizing synapse formation in arborizing optic axons in vivo: dynapmics and modulation by BDNF. Nature Neuroscience, 4:1093-1101 (2001).
29. S. Cohen-Gory: The developing synapse: Construction and modulation of synaptic structures and circuits. Science, 298:770-776 (2002).
30. V. Askanas, H. Kwan, R. B. Alvarez, W. K. Engel, T. Kobayashi, A. Martinuzzi, E. F. Hawkins De novo neuromuscular junction formation on human muscle fibres cultured in monolayer and innervated by foetal rat spinal cord: Ultrastructural and ultrastructural-cytochemical studies. Journal of Neurocytology, 16:523-537 (1987).
31. Z. Grubic, R. Komel, W. F. Walker, A. F. Miranda: Myoblast fusion and innervation with rat motor nerve alter distribution of acetylcholinesterase and its mRNA in cultures of human muscle. Neuron, 14:317-327 (1995).
32. T. Kobayashi, V. Askanas: Acetylcholine receptors and acetylcholinesterase accumulate at the nerve-muscle contacts of de novo grown human monolayer muscle cocultured with fetal rat spinal cord. Experimental Neurology, 88:327-335 (1985).
33. E. Bandi, M. Jevsek, T. Mars, M. Jurdana, E. Formaggio, M. Sciancalepore, G. Fumagalli, Z. Grubic, F. Ruzzier, P. Lorenzon: Neural agrin controls maturation of the excitation-contraction coupling mechanism in human myotubes developing in vitro. Am J Physiol Cell Physiol, 294:C66-73 (2008).
34. M. Jurdana, G. Fumagalli, Z. Grubic, P. Lorenzon, T. Mars, M. Sciancalepore: Neural agrin changes the electrical properties of developing human skeletal muscle cells. Cellular & Molecular Neurobiology, 29:123-131 (2009).

35. N. Gajsek, M. Jevsek, Z. Grubic: Expression of MuSK in in vitro innervated human muscle. Journal of Molecular Neuroscience, 30:27-28 (2006).
36. M. Jevsek, T. Mars, K. Mis, Z. Grubic: Origin of acetylcholinesterase in the neuromuscular junction formed in the in vitro innervated human muscle. European Journal of Neuroscience, 20:2865-2871 (2004).
37. G.-S. Séverine, C. Gilliane, B. Serge, W. Jean-Marie, P. Philippe: Muscle could be the therapeutic target in SMA treatment. Journal of Neuroscience Research, 53:663-669 (1998).
38. B. J. Spargo, M. A. Testoff, T. B. Nielsen, D. A. Stenger, J. J. Hickman, A. S. Rudolph: Spatially controlled adhesion, spreading, and differentiation of endothelial cells on self-assembled molecular monolayers. Proc Natl Acad Sci USA, 91:11070-11074. (1994).
39. M. Das, P. Molnar, C. Gregory, L. Riedel, J. J. Hickman: Long-term culture of embryonic rat cardiomyocytes on an organosilane surface in a serum free medium. Biomaterials, 25:5643-5647 (2004).
40. M. S. Ravenscroft, K. E. Bateman, K. M. Shaffer, H. M. Schessler, D. R. Jung, T. W. Schneider, C. B. Montgomery, T. L. Custer, A. E. Schaffner, Q. Y. Liu, Y. X. Li, J. L. Barker, J. J. Hickman: Developmental neurobiology implications from fabrication and analysis of hippocampal neuronal networks on patterned silane-modified surfaces. Journal of the American Chemical Society, 120:12169-12177 (1998).
41. D. A. Stenger, J. J. Hickman, K. E. Bateman, M. S. Ravenscroft, W. Ma, J. J. Pancrazio, K. Shaffer, A. E. Schaffner, D. H. Cribbs, C. W. Cotman: Microlithographic determination of axonal/dendritic polarity in cultured hippocampal neurons. J Neurosci Methods, 82:167-173. (1998).
42. M. Das, N. Bhargava, C. Gregory, L. Riedel, P. Molnar, J. J. Hickman: Adult rat spinal cord culture on an organosilane surface in a novel serum-free medium. In vitro Cellular & Developmental Biology—Animal, 41:343348 (2005).
43. M. Das, J. W. Rumsey, C. A. Gregory, N. Bhargava, J. F. Kang, P. Molnar, L. Riedel, J. J. Hickman: Embryonic motor neuron-skeletal muscle coculture in a defined system. Neuroscience, 146:481-488 (2007).
44. D. Cizkova, O. Kakinohana, K. Kucharova, S. Marsala, K. Johe, T. Hazel, M. P. Hefferan, M. Marsala: Functional recovery in rats with ischemic paraplegia after spinal grafting of human spinal stem cells. Neuroscience, 147:546-560 (2007).
45. L. Xu, J. Yan, D. Chen, A. M. Welsh, T. Hazel, K. Johe, G. Hatfield, V. E. Koliatsos: Human neural stem cell grafts ameliorate motor neuron disease in SOD-1 transgenic rats. Transplantation, 82:865-875 (2006).
46. J. Yan, L. Xu, A. M. Welsh, G. Hatfield, T. Hazel, K. Johe, V. E. Koliatsos: Extensive neuronal differentiation of human neural stem cell grafts in adult rat spinal cord. PLoS Medicine, 4:318-332 (2007).
47. L. Thorrez, J. Shansky, L. Wang, L. Fast, T. Vanden-Driessche, M. Chuah, D. Mooney, H. Vandenburgh: Growth, differentiation, transplantation and survival of human skeletal myofibers on biodegradable scaffolds. Biomaterials, 29:75-84 (2008).
48. J. V. Hennessey, J. A. Chromiak, S. Dellaventura, J. Guertin, D. B. Maclean: Increase in percutaneous muscle biopsy yield with a suction-enhancement technique. Journal of Applied Physiology, 82:1739-1742 (1997).
49. C. Powell, J. Shansky, M. DelTatto, D. E. Forman, J. Hennessey, K. Sullivan, B. A. Zielinski, H. H. Vandenburgh: Tissue engineered human bioartificial muscles expressing a foreign recombinant protein for gene therapy. Human Gene Therapy, 10:565-577 (1999).
50. B. X. Gao, L. Ziskind-Conhaim: Development of ionic currents underlying changes in action potential waveforms in rat spinal motoneurons. Journal of Neurophysiology, 80:3047-3061 (1998).
51. B. X. Gao, L. Ziskind-Conhaim: Development of Glycine- and GABA-gated currents in rat spinal motoneurons. J Neurophysiology, 74:113-121 (1995).
52. T. Takahashi: Intracellular recording from visually identified motoneurons in rat spinal cord slices. Proc R Soc Lond B Biol Sci, 202:417-421 (1978).
53. Brewer, G. J., Boehler, M. D., Jones, T. T., and Wheeler, B. C. NbActiv4 medium improvement to Neurobasal/B27 increases neuron synapse densities and network spike rates on multielectrode arrays. J Neurosci Methods 170, 181, 2008.
54. Goritz, C., Mauch, D. H., and Pfrieger, F. W. Multiple mechanisms mediate cholesterol-induced synaptogenesis in a CNS neuron. Mol & Cell Neurosci 29, 190, 2005.
55. Pfrieger, F. W., and Barres, B. A. Synaptic efficacy enhanced by glial cells in vitro. Science 277, 1684, 1997.
56. Sasahara, K., Shikimi, H., Haraguchi, S., Sakamoto, H., Honda, S., Harada, N., and Tsutsui, K. Mode of action and functional significance of estrogen-inducing dendritic growth, spinogenesis, and synaptogenesis in the developing Purkinje cell. J Neurosci 27, 7408, 2007.
57. Fox, M. A., Sanes, J. R., Borza, D. B., Eswarakuma, V. P., Fassler, R., Hudson, B. G., John, S. W. M., Ninomiya, Y., Pedchenko, V., Pfaff, S. L., Rheault, M. N., Sado, Y., Segal, Y., Werle, M., and Umemori, H. Distinct target-derived signals organize formation, maturation, and maintenance of motor nerve terminals. Cell 129, 179, 2007.
58. Janne J, Johan H, Petter B. Human embryonic stem cell technologies and drug discovery. Journal of Cellular Physiology 2009; 219(3): 513-519.
59. Cai J, Zhao Y, Liu Y, Ye F, Song Z, Qin H, et al. Directed differentiation of human embryonic stem cells into functional hepatic cells. Hepatology 2007; 45(5): 1229-1239.
60. Guenou H, Nissan X, Larcher F, Feteira J, Lemaitre G, Saidani M, et al. Human embryonic stem-cell derivatives for full reconstruction of the pluristratified epidermis: A preclinical study. The Lancet 2009; 374 (9703) 1745-1753.
61. Schlüter H, Kaur P. Bioengineered human skin from embryonic stem cells. The Lancet 2009; 374(9703): 1725-1726.
62. Vidarsson H, Hyllner J, Sartipy P. Differentiation of human embryonic stem cells to cardiomyocytes for in vitro and in vivo applications. Stem Cell Reviews and Reports 2010; 6(1): 108-120.
63. White S M, Claycomb W C. Embryonic stem cells form an organized, functional cardiac conduction system in vitro. Am J Physiol Heart Circ Physiol 2005; 288(2): H670-679.
64. Boillée S, Velde C V, Cleveland D W. Als: A disease of motor neurons and their normeuronal neighbors. Neuron 2006; 52(1): 39-59.
65. Stavarachi M, Apostol P, Toma M, Cimponeriu D, Gavrilla L. Spinal muscular atrophy disease: A literature review for therapeutic strategies. Journal of Medicine and Life 2010; 3(1): 3-9.
66. Emery A E H. The muscular dystrophies. The Lancet 2002; 359(9307): 687-695.

TABLE 1

Composition of Enriched Co-culture Media.

| Component | Full Name | Concentration | Company | Catalog Number |
|---|---|---|---|---|
| NEUROBASAL ™/ NEUROBASAL ™ A | | | Invitrogen | 10888/21103 |
| 827 (50X) | | 1X | Invitrogen | 17504-044 |
| Glutamax (100X) | | 1X | Invitrogen | 35050 |
| GDNF | Glial-derived Neurotrophic Factor | 10 ng/ml | Cell Sciences | CRG400B |
| BDNF | Brain-derived Neurotrophic Factor | 20 ng/ml | Cell Sciences | CRB600B |
| Shh | Sonic Hedgehog, N- terminal peptide | 50 ng/ml | R&D | 1845-SH-025 |
| RA | Retinoic Acid | 0.1 uM | Sigma | R2625 |
| IGF-1 | Insulin-like Growth Factor -1 | 10 ng/ml | PeproTech | 100-11 |
| cAMP | Adenosine 3',5'-cyclic Monophosphate | 1 uM | Sigma | A9501 |
| CNTF | Ciliary Neurotrophic Factor | 5 ng/ml | Cell Sciences | CRC400A |
| NT-3 | Neurotrophin-3 | 20 ng/ml | Cell Sciences | CRN500B |
| NT-4 | Neurotrophin-4 | 20 ng/ml | Cell Sciences | CRN501B |
| Vitronectin | | 100 ng/ml | Sigma | V8379 |
| Laminin | Mouse Laminin | 4 µg/ml | Invitrogen | 23017-015 |
| G5 (100X) | | 1X | Invitrogen | 17503-012 |
| Agrin | | 100 ng/ml | R&D | 550-AG-100 |

The invention claimed is:

1. A method of screening for a candidate therapeutic drug for a neuromuscular disease, the method comprising:
co-culturing differentiated human skeletal muscle stem cells adhered to an artificial surface and overlayered with differentiated human spinal cord stem cells in a serum-free medium;
forming at least one functional neuromuscular junction between a differentiated human skeletal muscle stem cell and a differentiated human spinal cord stem cell;
contacting the at least one functional neuromuscular junction with a candidate drug;
and monitoring the at least one functional neuromuscular junction following contact with the candidate drug, wherein the monitoring comprises recording one or more electrophysiological properties of the co-culture or video recording of the co-culture.

2. The method of claim 1, further comprising comparing the one or more electrophysiological properties of the co-culture after the contacting step to the same one or more electrophysiological properties of the co-culture before the contacting step.

3. The method of claim 2, wherein a change in the one or more electrophysiological properties of the co-culture indicates a candidate drug.

4. The method of claim 3, wherein the candidate drug affects neuromuscular junction synaptogenesis.

5. The method of claim 3, wherein the candidate drug affects neuronal initiation of muscle contraction.

6. The method of claim 1, wherein recording one or more electrophysiological properties comprises a current-clamp technique, a voltage-clamp technique, or both.

7. The method of claim 1, wherein the serum-free medium comprises the components in Table 1.

8. The method of claim 1, wherein the serum-free medium comprises at least one synaptogenesis promoting component and one or more trophic factors.

9. The method of claim 1, wherein the serum-free medium comprises NbActiv4.

10. The method of claim 1, wherein the artificial surface comprises a silicon based substrate monolayer deposited thereon.

11. The method of claim 10, wherein the silicon based substrate monolayer comprises DETA (trimethoxysilylpropyldiethylenetri-amine).

12. The method of claim 10, wherein the silicon based substrate monolayer is deposited on the artificial surface in a predetermined pattern.

13. The method of claim 1, wherein the method is a high-throughput screening method.

* * * * *